US012396907B2

(12) United States Patent
Heimbrock et al.

(10) Patent No.: US 12,396,907 B2
(45) Date of Patent: *Aug. 26, 2025

(54) BED INTERFACE FOR MANUAL LOCATION

(71) Applicant: Hill-Rom Services, Inc., Batesville, IN (US)

(72) Inventors: Richard H. Heimbrock, Cincinnati, OH (US); Jennifer A. Gunn, Durham, NC (US); John S. Schroder, Apex, NC (US); Hubert Lechable, Pluneret (FR); Jean-Marie Remoleur, Sainte Ann d'Auray (FR); Jimmy Samson, Pluvigner (FR); Richard J. Schuman, Cary, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/421,237

(22) Filed: Jan. 24, 2024

(65) Prior Publication Data
US 2024/0156658 A1    May 16, 2024

Related U.S. Application Data

(63) Continuation of application No. 16/930,427, filed on Jul. 16, 2020, now Pat. No. 11,911,325, which is a
(Continued)

(51) Int. Cl.
*G06F 3/048* (2013.01)
*A61B 5/00* (2006.01)
(Continued)

(52) U.S. Cl.
CPC .............. *A61G 7/05* (2013.01); *A61B 5/0004* (2013.01); *A61B 5/1115* (2013.01); *A61B 5/117* (2013.01);
(Continued)

(58) Field of Classification Search
None
See application file for complete search history.

(56) References Cited

U.S. PATENT DOCUMENTS

| | | |
|---|---|---|
| 1,758,546 A | 5/1930 | Wartmann |
| 2,330,356 A | 9/1943 | Belliveau |
| (Continued) | | |

OTHER PUBLICATIONS

Extended European Search Report for European Patent Application No. 20157521.4 dated Jul. 8, 2020 (9 pages).
(Continued)

*Primary Examiner* — Hua Lu
(74) *Attorney, Agent, or Firm* — Barnes & Thornburg LLP

(57) ABSTRACT

A graphical user interface (GUI) of a patient bed is used by a caregiver to manually enter location data indicative of a location in a healthcare facility at which the patient bed is located. A first screen for manually entering location data is displayed on the GUI after a threshold period of time elapses subsequent to a power plug of the patient bed being plugged into an alternating current (AC) outlet of the healthcare facility and subsequent to casters of the patient bed being braked. A voice prompt is also given from the patient bed after the threshold period of time elapses to remind the caregiver to manually enter the location data. After manual entry of the location data, circuitry of the patient bed transmits the location data entered by the caregiver and a bed identification (ID) from the bed for receipt by a remote computer for purposes of making a bed-to-room association.

24 Claims, 12 Drawing Sheets

Related U.S. Application Data continuation-in-part of application No. 16/743,340, filed on Jan. 15, 2020, now abandoned.

(60) Provisional application No. 62/810,445, filed on Feb. 26, 2019.

(51) Int. Cl.

| | |
|---|---|
| *A61B 5/11* | (2006.01) |
| *A61B 5/117* | (2016.01) |
| *A61G 7/05* | (2006.01) |
| *G01G 19/44* | (2006.01) |
| *G01G 19/52* | (2006.01) |
| *G06F 3/04817* | (2022.01) |
| *G06F 3/0482* | (2013.01) |
| *G06F 3/04847* | (2022.01) |
| *G16H 10/60* | (2018.01) |
| *G16H 40/20* | (2018.01) |
| *H04W 88/08* | (2009.01) |

(52) U.S. Cl.
CPC ......... *A61G 7/0527* (2016.11); *G01G 19/445* (2013.01); *G01G 19/52* (2013.01); *G06F 3/04817* (2013.01); *G06F 3/0482* (2013.01); *G06F 3/04847* (2013.01); *G16H 10/60* (2018.01); *G16H 40/20* (2018.01); *A61G 2203/12* (2013.01); *A61G 2203/16* (2013.01); *A61G 2203/20* (2013.01); *A61G 2205/20* (2013.01); *H04W 88/08* (2013.01)

(56) References Cited

U.S. PATENT DOCUMENTS

| | | |
|---|---|---|
| 2,335,524 A | 11/1943 | Lomax |
| 2,736,888 A | 2/1956 | McLain |
| 2,896,021 A | 7/1959 | Philipps |
| D188,659 S | 8/1960 | Locke |
| 3,054,201 A | 9/1962 | Burns |
| 3,098,220 A | 7/1963 | De Graaf |
| 3,181,141 A | 4/1965 | Villiers |
| 3,439,320 A | 4/1969 | Ward |
| 3,478,344 A | 11/1969 | Schwitzgebel et al. |
| 3,553,383 A | 1/1971 | Rochtus |
| 3,599,199 A | 8/1971 | Bunting |
| 3,599,200 A | 8/1971 | Bunting |
| 3,659,586 A | 5/1972 | Johns et al. |
| 3,696,384 A | 10/1972 | Lester |
| 3,739,329 A | 6/1973 | Lester |
| 3,767,859 A | 10/1973 | Doering et al. |
| 3,805,227 A | 4/1974 | Lester |
| 3,805,265 A | 4/1974 | Lester |
| 3,810,136 A | 5/1974 | Lang et al. |
| 3,913,153 A | 10/1975 | Adams et al. |
| 3,973,200 A | 8/1976 | Åkerberg |
| 4,052,567 A | 10/1977 | MacKay |
| 4,067,005 A | 1/1978 | Levy et al. |
| 4,126,768 A | 11/1978 | Grenzow |
| 4,150,284 A | 4/1979 | Trenkler et al. |
| 4,151,407 A | 4/1979 | McBride et al. |
| 4,183,015 A | 1/1980 | Drew et al. |
| 4,216,462 A | 8/1980 | McGrath et al. |
| 4,224,596 A | 9/1980 | Knickel |
| 4,225,953 A | 9/1980 | Simon et al. |
| 4,228,426 A | 10/1980 | Roberts |
| 4,237,344 A | 12/1980 | Moore |
| 4,264,982 A | 4/1981 | Sakarya |
| 4,275,385 A | 6/1981 | White |
| 4,279,433 A | 7/1981 | Petaja |
| 4,298,863 A | 11/1981 | Natitus et al. |
| 4,331,953 A | 5/1982 | Blevins et al. |
| 4,356,475 A | 10/1982 | Neumann et al. |
| 4,363,029 A | 12/1982 | Piliavin et al. |
| 4,363,137 A | 12/1982 | Salisbury |
| 4,418,334 A | 11/1983 | Burnett |
| 4,455,548 A | 6/1984 | Burnett |
| 4,489,387 A | 12/1984 | Lamb et al. |
| 4,491,947 A | 1/1985 | Frank |
| 4,495,495 A | 1/1985 | Ormanns et al. |
| 4,495,496 A | 1/1985 | Miller, III |
| 4,532,419 A | 7/1985 | Takeda |
| 4,539,560 A | 9/1985 | Fleck et al. |
| 4,556,932 A | 12/1985 | Lehrer et al. |
| 4,577,060 A | 3/1986 | Webb et al. |
| 4,577,185 A | 3/1986 | Andersen |
| 4,578,671 A | 3/1986 | Flowers |
| 4,593,273 A | 6/1986 | Narcisse |
| 4,598,275 A | 7/1986 | Ross et al. |
| 4,601,064 A | 7/1986 | Shipley |
| 4,638,313 A | 1/1987 | Sherwood, Jr. et al. |
| 4,648,123 A | 3/1987 | Schrock |
| 4,649,385 A | 3/1987 | Aires et al. |
| 4,654,629 A | 3/1987 | Bezos et al. |
| 4,663,625 A | 5/1987 | Yewen |
| 4,677,599 A | 6/1987 | Obayashi et al. |
| 4,680,790 A | 7/1987 | Packard et al. |
| 4,688,026 A | 8/1987 | Scribner et al. |
| 4,699,149 A | 10/1987 | Rice |
| 4,706,689 A | 11/1987 | Man |
| 4,709,330 A | 11/1987 | Yokoi et al. |
| 4,740,788 A | 4/1988 | Konneker |
| 4,748,668 A | 5/1988 | Shamir et al. |
| 4,752,951 A | 6/1988 | Konneker |
| 4,792,798 A | 12/1988 | Wilowski |
| 4,795,905 A | 1/1989 | Zierhut |
| 4,803,599 A | 2/1989 | Trine et al. |
| 4,814,751 A | 3/1989 | Hawkins et al. |
| 4,833,452 A | 5/1989 | Currier |
| 4,833,467 A | 5/1989 | Kobayashi et al. |
| 4,835,372 A | 5/1989 | Gombrich et al. |
| 4,837,568 A | 6/1989 | Snaper |
| 4,839,975 A | 6/1989 | Elmer |
| 4,843,640 A | 6/1989 | Juengel |
| 4,849,615 A | 7/1989 | Mollet |
| 4,853,692 A | 8/1989 | Wolk et al. |
| 4,857,716 A | 8/1989 | Gombrich et al. |
| 4,862,088 A | 8/1989 | Etienne et al. |
| 4,871,997 A | 10/1989 | Adriaenssens et al. |
| 4,899,135 A | 2/1990 | Ghahariiran |
| 4,947,152 A | 8/1990 | Hodges |
| 4,955,000 A | 9/1990 | Nastrom |
| 4,958,645 A | 9/1990 | Cadell et al. |
| 4,967,195 A | 10/1990 | Shipley |
| 4,980,679 A | 12/1990 | Klaubert |
| 4,990,892 A | 2/1991 | Guest et al. |
| 4,998,095 A | 3/1991 | Shields |
| 4,998,939 A | 3/1991 | Potthast et al. |
| 5,005,005 A | 4/1991 | Brossia et al. |
| 5,006,830 A | 4/1991 | Merritt |
| 5,014,040 A | 5/1991 | Weaver et al. |
| 5,027,314 A | 6/1991 | Linwood et al. |
| 5,031,156 A | 7/1991 | Watts et al. |
| 5,041,086 A | 8/1991 | Koenig et al. |
| 5,062,151 A | 10/1991 | Shipley |
| 5,065,154 A | 11/1991 | Kaiser et al. |
| 5,079,808 A | 1/1992 | Brown |
| 5,086,290 A | 2/1992 | Murray et al. |
| 5,103,108 A | 4/1992 | Crimmins |
| 5,119,104 A | 6/1992 | Heller |
| 5,124,991 A | 6/1992 | Allen |
| 5,131,040 A | 7/1992 | Knapczyk |
| 5,137,033 A | 8/1992 | Norton |
| 5,153,584 A | 10/1992 | Engira |
| 5,164,886 A | 11/1992 | Chang |
| 5,164,985 A | 11/1992 | Nysen et al. |
| 5,217,003 A | 6/1993 | Wilk |
| 5,231,273 A | 7/1993 | Caswell et al. |
| 5,266,944 A | 11/1993 | Carroll et al. |
| 5,274,311 A | 12/1993 | Littlejohn et al. |
| 5,276,496 A | 1/1994 | Heller et al. |
| 5,283,781 A | 2/1994 | Buda et al. |
| 5,291,399 A | 3/1994 | Chaco |
| 5,317,309 A | 5/1994 | Vercellotti et al. |

(56) References Cited

U.S. PATENT DOCUMENTS

| | | |
|---|---|---|
| 5,319,191 A | 6/1994 | Crimmins |
| 5,319,355 A | 6/1994 | Russek |
| 5,319,363 A | 6/1994 | Welch et al. |
| 5,334,851 A | 8/1994 | Good et al. |
| 5,339,259 A | 8/1994 | Puma et al. |
| 5,341,126 A | 8/1994 | Boykin |
| 5,351,149 A | 9/1994 | Crimmins |
| 5,355,222 A | 10/1994 | Heller et al. |
| 5,357,254 A | 10/1994 | Kah, Jr. |
| 5,363,425 A | 11/1994 | Mufti et al. |
| 5,375,604 A | 12/1994 | Kelly et al. |
| 5,387,993 A | 2/1995 | Heller et al. |
| 5,396,224 A | 3/1995 | Dukes et al. |
| 5,396,227 A | 3/1995 | Carroll et al. |
| 5,402,469 A | 3/1995 | Hopper et al. |
| 5,416,695 A | 5/1995 | Stutman et al. |
| 5,421,177 A | 6/1995 | Sieber et al. |
| 5,434,775 A | 7/1995 | Sims et al. |
| 5,446,678 A | 8/1995 | Saltzstein et al. |
| RE35,035 E | 9/1995 | Shipley |
| 5,455,560 A | 10/1995 | Owen |
| 5,455,851 A | 10/1995 | Chaco et al. |
| 5,458,123 A | 10/1995 | Unger |
| 5,461,390 A | 10/1995 | Hoshen |
| 5,465,082 A | 11/1995 | Chaco |
| 5,471,404 A | 11/1995 | Mazer |
| 5,475,367 A | 12/1995 | Prevost |
| 5,482,036 A | 1/1996 | Diab et al. |
| 5,515,426 A | 5/1996 | Yacenda et al. |
| 5,519,380 A | 5/1996 | Edwards |
| 5,534,851 A | 7/1996 | Russek |
| 5,534,876 A | 7/1996 | Erickson et al. |
| 5,537,459 A | 7/1996 | Price et al. |
| 5,548,637 A | 8/1996 | Heller et al. |
| 5,549,113 A | 8/1996 | Halleck et al. |
| 5,561,412 A | 10/1996 | Novak et al. |
| 5,568,119 A | 10/1996 | Schipper et al. |
| 5,572,195 A | 11/1996 | Heller et al. |
| 5,576,952 A | 11/1996 | Stutman et al. |
| 5,579,001 A | 11/1996 | Dempsey et al. |
| 5,588,005 A | 12/1996 | Ali et al. |
| 5,594,786 A | 1/1997 | Chaco et al. |
| 5,621,388 A | 4/1997 | Sherburne et al. |
| 5,627,524 A | 5/1997 | Fredrickson et al. |
| 5,629,678 A | 5/1997 | Gargano et al. |
| 5,633,742 A | 5/1997 | Shipley |
| 5,635,907 A | 6/1997 | Bernard et al. |
| 5,636,245 A | 6/1997 | Ernst et al. |
| 5,639,393 A | 6/1997 | Veltum et al. |
| 5,640,002 A | 6/1997 | Ruppert et al. |
| 5,640,146 A | 6/1997 | Campana, Jr. |
| 5,640,953 A | 6/1997 | Bishop et al. |
| 5,650,769 A | 7/1997 | Campana, Jr. |
| 5,650,770 A | 7/1997 | Schlager et al. |
| 5,661,457 A | 8/1997 | Ghaffari et al. |
| 5,664,035 A | 9/1997 | Tsuji et al. |
| 5,664,270 A | 9/1997 | Bell et al. |
| 5,682,139 A | 10/1997 | Pradeep et al. |
| 5,686,888 A | 11/1997 | Welles, II et al. |
| 5,686,902 A | 11/1997 | Reis et al. |
| 5,687,109 A | 11/1997 | Protigal et al. |
| 5,687,735 A | 11/1997 | Dempsey et al. |
| 5,689,229 A | 11/1997 | Chaco et al. |
| 5,691,980 A | 11/1997 | Welles, II et al. |
| 5,699,038 A | 12/1997 | Ulrich et al. |
| 5,705,980 A | 1/1998 | Shapiro |
| 5,708,421 A | 1/1998 | Boyd |
| 5,708,423 A | 1/1998 | Ghaffari et al. |
| 5,713,856 A | 2/1998 | Eggers et al. |
| 5,719,761 A | 2/1998 | Gatti et al. |
| 5,731,757 A | 3/1998 | Layson, Jr. |
| 5,742,237 A | 4/1998 | Bledsoe |
| 5,742,238 A | 4/1998 | Fox |
| 5,745,037 A | 4/1998 | Guthrie et al. |
| 5,748,148 A | 5/1998 | Heiser et al. |
| 5,751,246 A | 5/1998 | Hertel |
| 5,752,917 A | 5/1998 | Fuchs |
| 5,754,125 A | 5/1998 | Pearce |
| 5,760,704 A | 6/1998 | Barton et al. |
| 5,764,162 A | 6/1998 | Ehrlich |
| 5,767,788 A | 6/1998 | Ness |
| 5,767,791 A | 6/1998 | Stoop et al. |
| 5,771,003 A | 6/1998 | Seymour |
| 5,776,056 A | 7/1998 | Bu et al. |
| 5,781,442 A | 7/1998 | Engleson et al. |
| 5,781,632 A | 7/1998 | Odom |
| 5,792,063 A | 8/1998 | Danielsson et al. |
| 5,793,290 A | 8/1998 | Eagleson et al. |
| 5,808,564 A | 9/1998 | Simms et al. |
| 5,812,056 A | 9/1998 | Law |
| 5,822,418 A | 10/1998 | Yacenda et al. |
| 5,822,544 A * | 10/1998 | Chaco .................. G16H 40/63 340/286.07 |
| 5,828,306 A | 10/1998 | Curran |
| 5,831,533 A | 11/1998 | Kanno |
| 5,838,223 A | 11/1998 | Gallant et al. |
| 5,838,472 A | 11/1998 | Welch et al. |
| 5,844,488 A | 12/1998 | Musick |
| 5,867,821 A | 2/1999 | Ballantyne et al. |
| 5,877,675 A | 3/1999 | Rebstock et al. |
| 5,878,143 A | 3/1999 | Moore |
| 5,897,506 A | 4/1999 | Cohn |
| 5,898,459 A | 4/1999 | Smith et al. |
| 5,910,776 A | 6/1999 | Black |
| 5,933,488 A | 8/1999 | Marcus et al. |
| 5,936,527 A | 8/1999 | Isaacman et al. |
| 5,936,539 A | 8/1999 | Fuchs |
| 5,942,986 A | 8/1999 | Shabot et al. |
| 5,944,659 A | 8/1999 | Flach et al. |
| 5,956,660 A | 9/1999 | Neumann |
| 5,963,133 A | 10/1999 | Monjo |
| 5,963,137 A | 10/1999 | Waters, Sr. |
| 5,973,598 A | 10/1999 | Beigel |
| 5,974,389 A | 10/1999 | Clark et al. |
| 5,991,728 A | 11/1999 | DeBusk et al. |
| 5,995,937 A | 11/1999 | DeBusk et al. |
| 5,997,476 A | 12/1999 | Brown |
| RE36,530 E | 1/2000 | Heller et al. |
| 6,014,633 A | 1/2000 | DeBusk et al. |
| 6,026,818 A | 2/2000 | Blair et al. |
| 6,028,514 A | 2/2000 | Lemelson et al. |
| 6,031,458 A | 2/2000 | Jacobsen et al. |
| 6,031,459 A | 2/2000 | Lake |
| 6,031,460 A | 2/2000 | Banks |
| 6,034,603 A | 3/2000 | Steeves |
| 6,034,622 A | 3/2000 | Levine |
| 6,037,879 A | 3/2000 | Tuttle |
| 6,040,773 A | 3/2000 | Vega et al. |
| 6,049,278 A | 4/2000 | Guthrie et al. |
| 6,049,290 A | 4/2000 | Halstead |
| 6,052,710 A | 4/2000 | Saliba et al. |
| 6,054,927 A | 4/2000 | Brickell |
| 6,055,487 A | 4/2000 | Margery et al. |
| 6,055,506 A | 4/2000 | Frasca, Jr. |
| 6,057,758 A | 5/2000 | Dempsey et al. |
| 6,057,782 A | 5/2000 | Koenig |
| 6,067,019 A | 5/2000 | Scott |
| 6,069,555 A | 5/2000 | Skitek et al. |
| 6,069,564 A | 5/2000 | Hatano et al. |
| 6,069,570 A | 5/2000 | Herring |
| 6,075,707 A | 6/2000 | Ferguson et al. |
| 6,076,166 A | 6/2000 | Moshfeghi et al. |
| 6,078,251 A | 6/2000 | Landt et al. |
| 6,078,259 A | 6/2000 | Brady et al. |
| 6,078,261 A | 6/2000 | Davsko |
| 6,078,631 A | 6/2000 | Yabe et al. |
| RE36,791 E | 7/2000 | Heller |
| 6,084,512 A | 7/2000 | Elberty et al. |
| 6,085,069 A | 7/2000 | Sharpe |
| 6,085,493 A | 7/2000 | DeBusk et al. |
| 6,088,362 A | 7/2000 | Turnbull et al. |
| 6,091,332 A | 7/2000 | Eberhardt et al. |
| 6,091,530 A | 7/2000 | Duckworth |
| 6,093,146 A | 7/2000 | Filangeri |

(56) References Cited

U.S. PATENT DOCUMENTS

| | | |
|---|---|---|
| 6,097,301 A | 8/2000 | Tuttle |
| 6,097,308 A | 8/2000 | Albert et al. |
| 6,100,804 A | 8/2000 | Brady et al. |
| 6,101,390 A | 8/2000 | Jayaraman et al. |
| 6,104,295 A | 8/2000 | Gaisser et al. |
| 6,104,311 A | 8/2000 | Lastinger |
| 6,111,506 A | 8/2000 | Yap et al. |
| 6,114,962 A | 9/2000 | Wiklof et al. |
| 6,118,379 A | 9/2000 | Kodukula et al. |
| 6,127,928 A | 10/2000 | Issacman et al. |
| 6,130,612 A | 10/2000 | Castellano et al. |
| 6,133,832 A | 10/2000 | Winder et al. |
| 6,133,837 A | 10/2000 | Riley |
| 6,137,411 A | 10/2000 | Tyren |
| 6,137,412 A | 10/2000 | Herzer |
| 6,137,414 A | 10/2000 | Federman |
| 6,144,301 A | 11/2000 | Frieden |
| 6,144,303 A | 11/2000 | Federman |
| 6,147,592 A | 11/2000 | Ulrich et al. |
| 6,148,291 A | 11/2000 | Radican |
| 6,150,948 A | 11/2000 | Watkins |
| 6,150,950 A | 11/2000 | Shen Liu |
| 6,154,135 A | 11/2000 | Kane et al. |
| 6,154,139 A | 11/2000 | Heller |
| 6,157,302 A | 12/2000 | Kolton et al. |
| 6,160,881 A | 12/2000 | Beyda et al. |
| 6,169,484 B1 | 1/2001 | Schuchman et al. |
| 6,169,485 B1 | 1/2001 | Campana, Jr. |
| 6,177,861 B1 | 1/2001 | MacLellan et al. |
| 6,183,417 B1 | 2/2001 | Geheb et al. |
| 6,203,495 B1 | 3/2001 | Bardy |
| 6,204,765 B1 | 3/2001 | Brady et al. |
| 6,204,813 B1 | 3/2001 | Wadell et al. |
| 6,208,250 B1 | 3/2001 | Dixon et al. |
| 6,211,666 B1 | 4/2001 | Acker |
| 6,211,781 B1 | 4/2001 | McDonald |
| 6,211,796 B1 | 4/2001 | Toms et al. |
| 6,215,389 B1 | 4/2001 | Schmidt |
| 6,222,440 B1 | 4/2001 | Heller |
| 6,228,029 B1 | 5/2001 | Eccardt et al. |
| 6,236,319 B1 | 5/2001 | Pitzer et al. |
| 6,241,668 B1 | 6/2001 | Herzog |
| 6,249,234 B1 | 6/2001 | Ely et al. |
| 6,259,355 B1 | 7/2001 | Chaco et al. |
| 6,262,666 B1 | 7/2001 | Lodichand |
| 6,264,614 B1 | 7/2001 | Albert et al. |
| 6,268,797 B1 | 7/2001 | Berube et al. |
| 6,275,153 B1 | 8/2001 | Brooks |
| 6,279,183 B1 | 8/2001 | Kummer et al. |
| 6,280,409 B1 | 8/2001 | Stone et al. |
| 6,285,742 B1 | 9/2001 | Haumann et al. |
| 6,287,253 B1 | 9/2001 | Ortega et al. |
| 6,289,237 B1 | 9/2001 | Mickle et al. |
| 6,293,699 B1 | 9/2001 | Bailey et al. |
| 6,294,953 B1 | 9/2001 | Steeves |
| 6,302,844 B1 | 10/2001 | Walker et al. |
| 6,314,556 B1 | 11/2001 | DeBusk et al. |
| 6,320,510 B2 | 11/2001 | Menkedick et al. |
| RE37,467 E | 12/2001 | Brasch et al. |
| 6,333,690 B1 | 12/2001 | Nelson et al. |
| RE37,531 E | 1/2002 | Chaco et al. |
| 6,343,064 B1 | 1/2002 | Jabbarnezhad |
| 6,344,794 B1 | 2/2002 | Ulrich et al. |
| 6,348,777 B1 | 2/2002 | Brown et al. |
| 6,353,413 B1 | 3/2002 | White et al. |
| 6,362,725 B1 | 3/2002 | Ulrich et al. |
| 6,364,834 B1 | 4/2002 | Reuss et al. |
| 6,398,727 B1 | 6/2002 | Bui et al. |
| 6,400,956 B1 | 6/2002 | Richton |
| 6,406,426 B1 | 6/2002 | Reuss et al. |
| 6,407,335 B1 | 6/2002 | Franklin-Lees et al. |
| 6,412,980 B1 | 7/2002 | Lounsberry et al. |
| 6,416,471 B1 | 7/2002 | Kumar et al. |
| 6,418,416 B1 | 7/2002 | Rosenberg et al. |
| 6,421,649 B1 | 7/2002 | Rattner |
| 6,424,264 B1 | 7/2002 | Giraldin et al. |
| 6,439,769 B1 | 8/2002 | Polkus et al. |
| 6,441,742 B1 | 8/2002 | Lovely et al. |
| 6,442,290 B1 | 8/2002 | Ellis et al. |
| 6,445,299 B1 | 9/2002 | Rojas, Jr. |
| 6,450,956 B1 | 9/2002 | Rappaport et al. |
| 6,462,656 B2 | 10/2002 | Ulrich et al. |
| 6,486,792 B1 | 11/2002 | Moster et al. |
| 6,486,794 B1 | 11/2002 | Calistro et al. |
| 6,493,568 B1 | 12/2002 | Bell et al. |
| 6,494,831 B1 | 12/2002 | Koritzinsky |
| 6,510,344 B1 | 1/2003 | Halpern |
| 6,516,324 B1 | 2/2003 | Jones et al. |
| 6,526,310 B1 | 2/2003 | Carter et al. |
| 6,529,164 B1 | 3/2003 | Carter |
| 6,533,453 B1 | 3/2003 | Heidsieck et al. |
| 6,535,576 B2 | 3/2003 | Vafi et al. |
| 6,544,174 B2 | 4/2003 | West et al. |
| 6,551,243 B2 | 4/2003 | Bocionek et al. |
| 6,553,106 B1 | 4/2003 | Gould et al. |
| 6,554,174 B2 | 4/2003 | Aceves |
| 6,556,630 B1 | 4/2003 | Brinsfield et al. |
| 6,560,274 B1 | 5/2003 | Leitgeb et al. |
| 6,572,556 B2 | 6/2003 | Stoycos et al. |
| 6,575,901 B2 | 6/2003 | Stoycos et al. |
| 6,581,204 B2 | 6/2003 | DeBusk et al. |
| 6,584,182 B2 | 6/2003 | Brodnick |
| 6,584,454 B1 | 6/2003 | Hummel, Jr. et al. |
| 6,585,645 B2 | 7/2003 | Hutchinson |
| 6,589,170 B1 | 7/2003 | Flach et al. |
| 6,593,528 B2 | 7/2003 | Franklin-Lees et al. |
| 6,593,845 B1 | 7/2003 | Friedman et al. |
| 6,594,146 B2 | 7/2003 | Frangesch et al. |
| 6,594,519 B2 | 7/2003 | Stoycos et al. |
| 6,600,418 B2 | 7/2003 | Francis et al. |
| 6,600,421 B2 | 7/2003 | Freeman |
| 6,603,494 B1 | 8/2003 | Banks et al. |
| 6,609,115 B1 | 8/2003 | Mehring et al. |
| 6,616,606 B1 | 9/2003 | Petersen et al. |
| 6,622,088 B2 | 9/2003 | Hood |
| 6,640,246 B1 | 10/2003 | Gary, Jr. et al. |
| 6,643,238 B2 | 11/2003 | Nakajima |
| 6,650,346 B1 | 11/2003 | Jaeger et al. |
| 6,659,947 B1 | 12/2003 | Carter et al. |
| 6,665,385 B2 | 12/2003 | Rogers et al. |
| 6,665,820 B1 | 12/2003 | Frowein et al. |
| 6,669,630 B1 | 12/2003 | Joliat et al. |
| 6,671,547 B2 | 12/2003 | Lyster et al. |
| 6,671,563 B1 | 12/2003 | Engelson et al. |
| 6,685,633 B2 | 2/2004 | Albert et al. |
| 6,689,091 B2 | 2/2004 | Bui et al. |
| 6,693,513 B2 | 2/2004 | Tuttle |
| 6,693,514 B2 | 2/2004 | Perea, Jr. et al. |
| 6,694,367 B1 | 2/2004 | Miesbauer et al. |
| 6,694,509 B1 | 2/2004 | Stoval et al. |
| 6,697,765 B2 | 2/2004 | Kuth |
| 6,707,476 B1 | 3/2004 | Hochstedler |
| 6,714,913 B2 | 3/2004 | Brandt et al. |
| 6,721,818 B1 | 4/2004 | Nakamura |
| 6,726,634 B2 | 4/2004 | Freeman |
| 6,727,818 B1 | 4/2004 | Wildman et al. |
| 6,731,311 B2 | 5/2004 | Bufe et al. |
| 6,731,908 B2 | 5/2004 | Berliner et al. |
| 6,731,989 B2 | 5/2004 | Engleson et al. |
| 6,740,033 B1 | 5/2004 | Olejniczak et al. |
| 6,747,560 B2 | 6/2004 | Stevens, III |
| 6,747,562 B2 | 6/2004 | Giraldin et al. |
| 6,749,566 B2 | 6/2004 | Russ |
| 6,751,630 B1 | 6/2004 | Franks et al. |
| 6,754,545 B2 | 6/2004 | Haeuser et al. |
| 6,754,883 B2 | 6/2004 | DeBusk et al. |
| 6,756,918 B2 | 6/2004 | Fomukong |
| 6,759,959 B2 | 7/2004 | Wildman |
| 6,763,541 B2 | 7/2004 | Mahoney et al. |
| 6,771,172 B1 | 8/2004 | Robinson et al. |
| 6,773,396 B2 | 8/2004 | Flach et al. |
| 6,778,225 B2 | 8/2004 | David |
| 6,781,517 B2 | 8/2004 | Moster et al. |
| 6,784,797 B2 | 8/2004 | Smith et al. |

(56) References Cited

U.S. PATENT DOCUMENTS

| | | |
|---|---|---|
| 6,791,460 B2 | 9/2004 | Dixon et al. |
| 6,792,396 B2 | 9/2004 | Inda et al. |
| 6,798,533 B2 | 9/2004 | Tipirneni |
| 6,801,227 B2 | 10/2004 | Bocionek et al. |
| 6,807,543 B2 | 10/2004 | Muthya |
| 6,812,824 B1 | 11/2004 | Goldinger et al. |
| 6,825,763 B2 | 11/2004 | Ulrich et al. |
| 6,826,578 B2 | 11/2004 | Brackett et al. |
| 6,828,992 B1 | 12/2004 | Freeman et al. |
| 6,829,796 B2 | 12/2004 | Salvatini et al. |
| 6,830,549 B2 | 12/2004 | Bui et al. |
| 6,832,199 B1 | 12/2004 | Kucek et al. |
| 6,838,992 B2 | 1/2005 | Tenarvitz |
| 6,840,117 B2 | 1/2005 | Hubbard, Jr. |
| 6,843,415 B2 | 1/2005 | Vogler |
| 6,847,435 B2 | 1/2005 | Honda et al. |
| 6,847,814 B1 | 1/2005 | Vogeleisen |
| 6,859,761 B2 | 2/2005 | Bensky et al. |
| 6,868,256 B2 | 3/2005 | Dooley et al. |
| 6,871,211 B2 | 3/2005 | Labounty et al. |
| 6,873,884 B2 | 3/2005 | Brackett et al. |
| 6,876,303 B2 | 4/2005 | Reeder et al. |
| 6,876,985 B2 | 4/2005 | Kawanaka |
| 6,884,255 B1 | 4/2005 | Newton |
| 6,885,288 B2 | 4/2005 | Pincus |
| 6,891,909 B2 | 5/2005 | Hurley et al. |
| 6,897,780 B2 | 5/2005 | Ulrich et al. |
| 6,904,161 B1 | 6/2005 | Becker et al. |
| 6,909,995 B2 | 6/2005 | Shiraishi |
| 6,912,549 B2 | 6/2005 | Rotter et al. |
| 6,915,170 B2 | 7/2005 | Engleson et al. |
| 6,925,367 B2 | 8/2005 | Fontius |
| 6,930,878 B2 | 8/2005 | Brackett et al. |
| 6,954,148 B2 | 10/2005 | Pulkkinen et al. |
| 6,958,706 B2 | 10/2005 | Chaco et al. |
| 6,968,194 B2 | 11/2005 | Aljadeff et al. |
| 6,972,682 B2 | 12/2005 | Lareau et al. |
| 6,988,989 B2 | 1/2006 | Weiner et al. |
| 6,998,985 B2 | 2/2006 | Reisman et al. |
| 6,998,986 B2 | 2/2006 | Smith |
| 7,002,468 B2 | 2/2006 | Eveland et al. |
| 7,003,443 B2 | 2/2006 | Ford et al. |
| 7,005,980 B1 | 2/2006 | Schmidt et al. |
| 7,009,495 B2 | 3/2006 | Hughes et al. |
| 7,009,516 B2 | 3/2006 | Enea |
| 7,014,100 B2 | 3/2006 | Zierolf |
| 7,019,663 B2 | 3/2006 | Sharony |
| 7,030,761 B2 | 4/2006 | Bridgelall et al. |
| 7,030,811 B2 | 4/2006 | Goren et al. |
| 7,034,684 B2 | 4/2006 | Boman et al. |
| 7,034,690 B2 | 4/2006 | Chaco |
| 7,035,818 B1 | 4/2006 | Bandy et al. |
| 7,038,573 B2 | 5/2006 | Bann |
| 7,038,584 B2 | 5/2006 | Carter |
| 7,038,588 B2 | 5/2006 | Boone et al. |
| 7,038,589 B2 | 5/2006 | Schmidt et al. |
| 7,042,358 B2 | 5/2006 | Moore |
| 7,042,361 B2 | 5/2006 | Kazdin et al. |
| 7,044,387 B2 | 5/2006 | Becker et al. |
| 7,046,153 B2 | 5/2006 | Oja et al. |
| 7,046,162 B2 | 5/2006 | Dunstan |
| 7,049,594 B2 | 5/2006 | Wu et al. |
| 7,053,779 B2 | 5/2006 | Thompson |
| 7,053,781 B1 | 5/2006 | Haire et al. |
| 7,053,831 B2 | 5/2006 | Dempsey et al. |
| 7,056,289 B2 | 6/2006 | Kasper et al. |
| 7,057,509 B2 | 6/2006 | Gualdi et al. |
| 7,061,366 B2 | 6/2006 | Bell et al. |
| 7,061,384 B2 | 6/2006 | Fujimoto |
| 7,062,455 B1 | 6/2006 | Tobey |
| 7,068,143 B2 | 6/2006 | Doering et al. |
| 7,071,820 B2 | 7/2006 | Callaway |
| 7,071,843 B2 | 7/2006 | Hashida et al. |
| 7,075,438 B2 | 7/2006 | Kent et al. |
| 7,080,061 B2 | 7/2006 | Kabala |
| 7,084,740 B2 | 8/2006 | Bridgelall |
| 7,091,879 B2 | 8/2006 | Swetlik et al. |
| 7,092,376 B2 | 8/2006 | Schuman |
| 7,099,895 B2 | 8/2006 | Dempsey |
| 7,102,510 B2 | 9/2006 | Boling et al. |
| 7,106,189 B2 | 9/2006 | Burneske et al. |
| 7,116,230 B2 | 10/2006 | Klowak |
| 7,117,027 B2 | 10/2006 | Zheng et al. |
| 7,138,913 B2 | 11/2006 | Mackenzie et al. |
| 7,142,112 B2 | 11/2006 | Buckingham et al. |
| 7,151,455 B2 | 12/2006 | Lindsay et al. |
| 7,152,791 B2 | 12/2006 | Chappidi et al. |
| 7,154,397 B2 | 12/2006 | Zerhusen et al. |
| 7,158,030 B2 | 1/2007 | Chung |
| 7,164,354 B1 | 1/2007 | Panzer |
| 7,165,040 B2 | 1/2007 | Ehrman et al. |
| 7,167,095 B2 | 1/2007 | Carrender |
| 7,170,407 B2 | 1/2007 | Wagner |
| 7,174,172 B2 | 2/2007 | Sharony et al. |
| 7,190,778 B2 | 3/2007 | Kucmerowski |
| 7,196,621 B2 | 3/2007 | Kochis |
| 7,199,716 B2 | 4/2007 | Shanks et al. |
| 7,202,785 B2 | 4/2007 | Maloney |
| 7,203,690 B2 | 4/2007 | Braun et al. |
| 7,209,790 B2 | 4/2007 | Thompson et al. |
| 7,218,231 B2 | 5/2007 | Higham |
| 7,225,241 B2 | 5/2007 | Yada |
| 7,230,536 B2 | 6/2007 | Shinada et al. |
| 7,242,306 B2 | 7/2007 | Wildman et al. |
| 7,242,308 B2 | 7/2007 | Ulrich et al. |
| 7,248,880 B2 | 7/2007 | Gheorghiu et al. |
| 7,248,933 B2 | 7/2007 | Wildman |
| 7,259,676 B2 | 8/2007 | Knadle, Jr. et al. |
| 7,265,668 B1 | 9/2007 | Brosius |
| 7,269,427 B2 | 9/2007 | Hoctor et al. |
| 7,277,048 B2 | 10/2007 | Hessing |
| 7,277,889 B2 | 10/2007 | Addonisio et al. |
| 7,283,046 B2 | 10/2007 | Culpepper et al. |
| 7,283,423 B2 | 10/2007 | Holm et al. |
| 7,286,868 B2 | 10/2007 | Govari |
| 7,292,151 B2 | 11/2007 | Ferguson et al. |
| 7,295,115 B2 | 11/2007 | Aljadeff et al. |
| 7,295,132 B2 | 11/2007 | Steiner |
| 7,298,359 B2 | 11/2007 | Kim et al. |
| 7,301,451 B2 | 11/2007 | Hastings |
| 7,304,577 B2 | 12/2007 | Waldner et al. |
| 7,304,578 B1 | 12/2007 | Sayers et al. |
| 7,304,579 B2 | 12/2007 | Diorio et al. |
| 7,307,522 B2 | 12/2007 | Dawson |
| 7,313,403 B2 | 12/2007 | Gong et al. |
| 7,315,248 B2 | 1/2008 | Egbert |
| 7,315,281 B2 | 1/2008 | Dejanovic et al. |
| 7,319,386 B2 | 1/2008 | Collins, Jr. et al. |
| 7,319,395 B2 | 1/2008 | Puzio et al. |
| 7,319,397 B2 | 1/2008 | Chung et al. |
| 7,319,412 B1 | 1/2008 | Coppinger et al. |
| 7,321,305 B2 | 1/2008 | Göllü |
| 7,333,018 B2 | 2/2008 | Singh et al. |
| 7,336,187 B2 | 2/2008 | Hubbard, Jr. et al. |
| 7,336,563 B2 | 2/2008 | Holm |
| 7,339,477 B2 | 3/2008 | Puzio et al. |
| 7,339,479 B2 | 3/2008 | Nishimura |
| 7,362,656 B2 | 4/2008 | Holm |
| 7,370,808 B2 | 5/2008 | Eastin |
| 7,375,648 B1 | 5/2008 | Mulka et al. |
| 7,375,654 B2 | 5/2008 | Culpepper et al. |
| 7,376,123 B2 | 5/2008 | Reuss |
| 7,394,385 B2 | 7/2008 | Franco, Jr. et al. |
| 7,411,509 B2 | 8/2008 | Rosenfeld et al. |
| 7,415,212 B2 | 8/2008 | Matsushita et al. |
| 7,417,544 B2 | 8/2008 | Artem et al. |
| 7,443,299 B2 | 10/2008 | Forster |
| 7,446,664 B2 | 11/2008 | White |
| 7,473,097 B2 | 1/2009 | Raby et al. |
| 7,474,224 B2 | 1/2009 | Long et al. |
| 7,515,044 B2 | 4/2009 | Welch et al. |
| 7,518,502 B2 | 4/2009 | Austin et al. |
| 7,538,679 B2 | 5/2009 | Shanks |
| 7,541,927 B2 | 6/2009 | Dupler et al. |

(56) References Cited

U.S. PATENT DOCUMENTS

| | | |
|---|---|---|
| 7,551,083 B2 | 6/2009 | Modes et al. |
| 7,567,794 B2 | 7/2009 | Dempsey |
| 7,598,853 B2 | 10/2009 | Becker et al. |
| 7,623,250 B2 | 11/2009 | Moctezuma de la Barrera et al. |
| 7,627,334 B2 | 12/2009 | Cohen et al. |
| 7,664,686 B2 | 2/2010 | Czyszczewski et al. |
| 7,667,572 B2 | 2/2010 | Husak et al. |
| RE41,236 E | 4/2010 | Seely |
| 7,714,728 B2 | 5/2010 | Koblasz |
| 7,724,147 B2 | 5/2010 | Brown |
| 7,725,195 B2 | 5/2010 | Lima et al. |
| 7,734,476 B2 | 6/2010 | Wildman et al. |
| 7,737,850 B2 | 6/2010 | Malik |
| 7,750,793 B2 | 7/2010 | Juels |
| 7,755,541 B2 | 7/2010 | Wisherd et al. |
| 7,756,723 B2 | 7/2010 | Rosow et al. |
| 7,761,320 B2 | 7/2010 | Fliess et al. |
| 7,765,286 B2 | 7/2010 | Mark |
| 7,800,914 B2 | 9/2010 | Dully |
| 7,844,505 B1 | 11/2010 | Arneson et al. |
| 7,848,760 B2 | 12/2010 | Caspi et al. |
| 7,869,861 B2 | 1/2011 | Moctezuma de la Barrera et al. |
| 7,890,349 B2 | 2/2011 | Cole et al. |
| 7,893,842 B2 | 2/2011 | Deutsch |
| 7,907,053 B2 | 3/2011 | Wildman et al. |
| 7,916,023 B2 | 3/2011 | Rado |
| 7,920,050 B2 | 4/2011 | Juels et al. |
| 7,928,844 B2 | 4/2011 | Mackenzie et al. |
| 7,933,780 B2 | 4/2011 | De La Huerga |
| 7,958,087 B2 | 6/2011 | Blumenau |
| 7,966,008 B2 | 6/2011 | Graves et al. |
| 8,026,821 B2 | 9/2011 | Reeder et al. |
| 8,031,057 B2 | 10/2011 | McNeely et al. |
| 8,073,558 B2 | 12/2011 | Koch et al. |
| 8,102,254 B2 | 1/2012 | Becker et al. |
| 8,160,677 B2 | 4/2012 | Gielen et al. |
| 8,164,444 B2 | 4/2012 | Anderson et al. |
| 8,190,730 B2 | 5/2012 | Dempsey |
| 8,223,009 B2 | 7/2012 | Anderson et al. |
| 8,248,467 B1 | 8/2012 | Ganick et al. |
| 8,272,892 B2 | 9/2012 | McNeely et al. |
| 8,284,047 B2 | 10/2012 | Collins, Jr. et al. |
| 8,310,364 B2 | 11/2012 | Derks et al. |
| 8,319,633 B2 | 11/2012 | Becker et al. |
| 8,321,302 B2 | 11/2012 | Bauer et al. |
| 8,334,898 B1 | 12/2012 | Ryan et al. |
| 8,334,901 B1 | 12/2012 | Ganick et al. |
| 8,390,462 B2 | 3/2013 | Belz et al. |
| 8,416,072 B2 | 4/2013 | Tenarvitz |
| 8,416,290 B2 | 4/2013 | Ryan et al. |
| 8,432,438 B2 | 4/2013 | Ryan et al. |
| 8,436,896 B2 | 5/2013 | Staats et al. |
| 8,447,626 B2 | 5/2013 | Sun et al. |
| 8,457,502 B2 | 6/2013 | Ryan et al. |
| 8,461,968 B2 | 6/2013 | Ball et al. |
| 8,461,982 B2 | 6/2013 | Becker et al. |
| 8,514,071 B2 | 8/2013 | Derks et al. |
| 8,516,514 B2 | 8/2013 | Belz et al. |
| 8,519,823 B2 | 8/2013 | Rinkes |
| 8,520,065 B2 | 8/2013 | Staats et al. |
| 8,558,660 B2 | 10/2013 | Nix et al. |
| 8,604,916 B2 | 12/2013 | McNeely et al. |
| 8,604,917 B2 | 12/2013 | Collins et al. |
| 8,610,562 B2 | 12/2013 | Weiner et al. |
| 8,650,045 B2 | 2/2014 | Baldock et al. |
| 8,674,826 B2 | 3/2014 | Becker et al. |
| 8,689,376 B2 | 4/2014 | Becker et al. |
| 8,752,045 B2 | 6/2014 | Fitzgerald et al. |
| 8,781,847 B2 | 7/2014 | Simms et al. |
| 9,020,963 B2 | 4/2015 | Goodman et al. |
| 9,026,301 B2 | 5/2015 | Zini et al. |
| 9,830,424 B2 | 11/2017 | Dixon et al. |
| 10,026,505 B2 | 7/2018 | Lack et al. |
| 11,911,325 B2 | 2/2024 | Heimbrock et al. |
| 2001/0050610 A1 | 12/2001 | Gelston |
| 2001/0051765 A1 | 12/2001 | Walker et al. |
| 2002/0044059 A1 | 4/2002 | Reeder et al. |
| 2002/0067273 A1 | 6/2002 | Jaques et al. |
| 2002/0070867 A1 | 6/2002 | Conway et al. |
| 2002/0165733 A1 | 11/2002 | Pulkkinen et al. |
| 2002/0173286 A1 | 11/2002 | Lindoff et al. |
| 2002/0173991 A1 | 11/2002 | Avitall |
| 2003/0010345 A1 | 1/2003 | Koblasz et al. |
| 2003/0028449 A1 | 2/2003 | Heinen et al. |
| 2003/0132845 A1 | 7/2003 | McDaniel, III |
| 2003/0149598 A1 | 8/2003 | Santoso et al. |
| 2003/0176798 A1 | 9/2003 | Simon |
| 2004/0024660 A1 | 2/2004 | Ganesh et al. |
| 2004/0106854 A1 | 6/2004 | Muraki |
| 2004/0186358 A1 | 9/2004 | Chernow et al. |
| 2005/0071198 A1 | 3/2005 | Krupa |
| 2005/0122119 A1 | 6/2005 | Barlow |
| 2005/0131729 A1 | 6/2005 | Melby et al. |
| 2006/0012474 A1 | 1/2006 | Lu et al. |
| 2006/0022818 A1 | 2/2006 | Piltonen |
| 2006/0028336 A1 | 2/2006 | Glenn et al. |
| 2006/0031259 A1 | 2/2006 | Gibson et al. |
| 2006/0038676 A1* | 2/2006 | Richards ............ G08B 21/0227 |
| | | 340/539.23 |
| 2006/0071774 A1 | 4/2006 | Brown et al. |
| 2006/0082444 A1 | 4/2006 | Sweeney, II et al. |
| 2006/0097863 A1 | 5/2006 | Horowitz et al. |
| 2006/0135083 A1 | 6/2006 | Leinonen et al. |
| 2006/0161214 A1 | 7/2006 | Patel |
| 2006/0220798 A1 | 10/2006 | Willis |
| 2006/0253590 A1 | 11/2006 | Nagy et al. |
| 2007/0005558 A1 | 1/2007 | Canfield |
| 2007/0015960 A1 | 1/2007 | Gornert et al. |
| 2007/0033072 A1 | 2/2007 | Bildirici |
| 2007/0073116 A1 | 3/2007 | Kiani et al. |
| 2007/0093879 A1 | 4/2007 | Bek et al. |
| 2007/0123173 A1 | 5/2007 | Stobbe |
| 2007/0129967 A1 | 6/2007 | Thompson et al. |
| 2007/0157385 A1 | 7/2007 | Lemire et al. |
| 2007/0271122 A1 | 11/2007 | Zaleski |
| 2008/0004993 A1 | 1/2008 | Horspool et al. |
| 2008/0026713 A1 | 1/2008 | Sekhar et al. |
| 2008/0040244 A1 | 2/2008 | Ricciuti et al. |
| 2008/0100706 A1 | 5/2008 | Breed |
| 2008/0106418 A1 | 5/2008 | Sloan et al. |
| 2008/0108372 A1 | 5/2008 | Breed |
| 2008/0126125 A1 | 5/2008 | Lichtenstein et al. |
| 2008/0126126 A1 | 5/2008 | Ballai |
| 2008/0136621 A1 | 6/2008 | Malik et al. |
| 2008/0136635 A1 | 6/2008 | Malik |
| 2008/0140544 A1 | 6/2008 | Ehrman et al. |
| 2008/0180322 A1 | 7/2008 | Islam et al. |
| 2008/0201388 A1 | 8/2008 | Wood et al. |
| 2008/0215360 A1* | 9/2008 | Dicks ................. A61M 5/003 |
| | | 705/2 |
| 2008/0238676 A1 | 10/2008 | Dhillon et al. |
| 2008/0242945 A1 | 10/2008 | Gugliotti et al. |
| 2008/0300918 A1 | 12/2008 | Tenenbaum et al. |
| 2008/0312974 A2 | 12/2008 | Rosow et al. |
| 2008/0312975 A2 | 12/2008 | Rosow et al. |
| 2009/0018882 A1 | 1/2009 | Burton et al. |
| 2009/0033500 A1 | 2/2009 | Malik et al. |
| 2009/0079549 A1 | 3/2009 | Ruder |
| 2009/0300507 A1 | 12/2009 | Raghavan et al. |
| 2010/0001838 A1 | 1/2010 | Miodownik et al. |
| 2010/0217618 A1 | 8/2010 | Piccirillo et al. |
| 2010/0289885 A1 | 11/2010 | Lu et al. |
| 2011/0050411 A1 | 3/2011 | Schuman et al. |
| 2011/0125513 A1 | 5/2011 | Tenarvitz et al. |
| 2011/0125524 A1 | 5/2011 | Tenarvitz et al. |
| 2011/0205061 A1* | 8/2011 | Wilson ................. G05B 19/042 |
| | | 340/573.1 |
| 2011/0208541 A1* | 8/2011 | Wilson ................. A61G 7/0527 |
| | | 705/2 |
| 2011/0227740 A1 | 9/2011 | Wohltjen |
| 2012/0089419 A1* | 4/2012 | Huster ................. A61G 7/015 |
| | | 705/3 |
| 2012/0124744 A1* | 5/2012 | Hornbach ............ A61G 7/16 |
| | | 5/613 |

(56) References Cited

U.S. PATENT DOCUMENTS

| | | | |
|---|---|---|---|
| 2012/0316892 A1 | 12/2012 | Huster et al. | |
| 2013/0069771 A1 | 3/2013 | Frondorf | |
| 2014/0066815 A1* | 3/2014 | Williamson | A61G 7/0513 |
| | | | 600/595 |
| 2014/0169795 A1* | 6/2014 | Clough | H04W 88/02 |
| | | | 398/106 |
| 2014/0207490 A1 | 7/2014 | Shindo et al. | |
| 2015/0033295 A1* | 1/2015 | Huster | G16H 40/67 |
| | | | 726/4 |
| 2015/0081335 A1 | 3/2015 | Dixon et al. | |
| 2015/0281659 A1* | 10/2015 | Hood | H04N 7/188 |
| | | | 348/143 |
| 2016/0136356 A1* | 5/2016 | Ribble | A61B 5/14552 |
| | | | 705/2 |
| 2016/0307429 A1* | 10/2016 | Hood | G08B 3/1016 |
| 2017/0027787 A1* | 2/2017 | Huster | A61G 7/0513 |
| 2018/0039743 A1* | 2/2018 | Dixon | H04W 4/029 |
| 2018/0161225 A1 | 6/2018 | Zerhusen et al. | |
| 2018/0185222 A1 | 7/2018 | Zerhusen et al. | |
| 2018/0296413 A1* | 10/2018 | Ribble | A61B 5/208 |
| 2020/0345568 A1 | 11/2020 | Heimbrock et al. | |

OTHER PUBLICATIONS

Office Action for U.S. Appl. No. 16/743,340 dated Apr. 29, 2021 (15 pages).
Amendment for U.S. Appl. No. 16/743,340 dated Jul. 21, 2021 (9 pages).
Final Office Action for U.S. Appl. No. 16/743,340 dated Aug. 5, 2021 (17 pages).
Amendment for U.S. Appl. No. 16/743,340 dated Sep. 27, 2021 (9 pages).
Office Action for U.S. Appl. No. 16/743,340 dated Feb. 17, 2022 (19 pages).
Amendment for U.S. Appl. No. 16/743,340 dated May 4, 2022 (10 pages).
Final Office Action for U.S. Appl. No. 16/743,340 dated May 26, 2022 (20 pages).
Amendment for U.S. Appl. No. 16/743,340 dated Jul. 19, 2022 (11 pages).
Chinese Office Action issued by the Chinese Intellectual Property Office dated Aug. 22, 2022 and its English translation (15 pages).
Advisory Action before the filing of an Appeal Brief and Examiner-Initiated Interview Summary for U.S. Appl. No. 16/743,340 dated Aug. 2, 2022 (4 pages).
Office Action for U.S. Appl. No. 16/743,340 dated Nov. 3, 2022 (19 pages).
Amendment for U.S. Appl. No. 16/743,340 dated Jan. 26, 2023 (10 pages).
Chinese Office Action issued by the Chinese Patent Office for Chinese Patent Application No. 2021107369642 dated Sep. 4, 2023 and its English translation (18 pages).
First Office Action issued by the Chinese Patent Office for Chinese Patent Application No. 2020100916329 dated Jan. 23, 2024 and its English translation (20 pages).

* cited by examiner

BED INTERFACE FOR MANUAL LOCATION

The present application is a continuation of U.S. application Ser. No. 16/930,427, filed Jul. 16, 2020, now U.S. Patent No. 11,911,325, which is a continuation-in-part of U.S. application Ser. No. 16/743,340, filed Jan. 15, 2020, which claims the benefit, under 35 U.S.C. § 119(e), of U.S. Provisional Application No. 62/810,445, filed Feb. 26, 2019, each of which is hereby incorporated by reference herein in its entirety.

BACKGROUND

The present disclosure relates to patient beds and particularly, to patient beds having equipment used in connection with determining locations of the patient beds in a healthcare facility. More particularly, the present disclosure relates to patient beds having bed interfaces for manual location of the patient beds.

Some healthcare facilities, such as hospitals, nursing homes, and the like, have nurse call systems that receive bed status data via a wired connection to a patient bed. For example, the NaviCare® Nurse Call system available from Hill-Rom Company, Inc. uses a 37-pin cable to interconnect patient beds to a bed interface unit (BIU) or network interface unit (NIU) or audio station bed connector (ASBC). The BTU's, NIU's, and ASBC's have identification (ID) codes such as serial numbers and/or MAC addresses that can be correlated with a room location in the healthcare facility. Thus, by connecting the patient beds to the respective BTU's, NIU's, or ASBC's, as the case may be, a remote computer device such as a server of the nurse call system is able to receive bed ID data and location ID data and determine the room locations of the various beds in the healthcare facility.

However, not all healthcare facilities have nurse call systems to which patient beds couple via a wired connection. In recent times, some patient beds are equipped with wireless communication circuitry for WiFi communication between the patient beds and wireless access points (WAP's) of the healthcare facility. The radio frequency (RF) signals from the WiFi circuitry of the patient beds is able to pass through walls, floors, and ceilings such that multiple WAP's may receive the RF signals transmitted from the beds. Accordingly, the room locations of such beds cannot be determined with absolute certainty based on which WAP's are able to communicate with the beds. What is needed, therefore, is an inexpensive way to determine the locations of patient beds having wireless communication capability but that are not coupled to nurse call systems via wired connections.

SUMMARY

An apparatus, system or method may comprise one or more of the features recited in the appended claims and/or the following features which, alone or in any combination, may comprise patentable subject matter:

According to a first aspect of the present disclosure, a patient bed may include a frame that may be configured to support a patient, circuitry that may be carried by the frame, and a graphical user interface (GUI) that may be carried by the frame and that may be coupled to the circuitry. The graphical user interface may display at least one user interface screen that may be used by a caregiver to manually enter location data that may be indicative of a location in a healthcare facility at which the patient bed may be located. The circuitry may be configured to transmit the location data entered by the caregiver and a bed identification (ID) from the bed. The circuitry may command the GUI to display a first screen of the at least one interface screen that may be used by the caregiver to manually enter location data. The first screen may be displayed after a threshold period of time may have elapsed subsequent to a power plug of the circuitry being plugged into an alternating current (AC) outlet of the healthcare facility and subsequent to casters of the frame being braked.

In some embodiments of the first aspect, the location data may include a room number of the healthcare facility. If desired, the GUI of the first aspect may include a change location button that may be selectable by the caregiver to initiate a change of the location data prior to the threshold period of time elapsing. A room menu screen may appear on the GUI in response to the change location button being selected. The room menu screen may permit the caregiver to select a room number from a list of room numbers. Alternatively or additionally, a campus icon and a unit icon may appear on the GUI in response to the change location button being selected. The campus icon may be selectable to cause a campus menu list to be displayed on the GUI and the unit icon may be selectable to cause a unit menu list to be displayed on the GUI.

The first screen appearing on the GUI after the threshold period of time may have elapsed may include a button that may be selectable to initiate manual entry of the location data. This button on the first screen is different than the change location button mentioned above. However, a room menu screen may appear on the GUI in response to the button being selected on the first screen. The room menu screen may permit the caregiver to select a room number from a list of room numbers. Alternatively or additionally, a campus icon and a unit icon may appears on the GUI in response to the button being selected on the first screen. The campus icon may be selectable to cause a campus menu list to be displayed on the GUI and the unit icon may be selectable to cause a unit menu list to be displayed on the GUI.

In some embodiments of the first aspect, the circuitry may include a wireless communication module that may be configured to wirelessly transmit the location data and the bed ID to a wireless access point for delivery to at least one remote computer for purposes of making a bed-to-room association. Optionally, the wireless communication module also may be configured to transmit bed status data from the bed. If desired, the circuitry may be configured to play a voice prompt to remind the caregiver to manually enter the location data after the threshold period of time may have elapsed.

According to a second aspect of the present disclosure, a patient bed may include a frame that may be configured to support a patient, circuitry that may be carried by the frame, and a graphical user interface (GUI) that may be carried by the frame and that may be coupled to the circuitry. The graphical user interface may display at least one user interface screen that may be used by a caregiver to manually enter location data that may be indicative of a location in a healthcare facility at which the patient bed may be located. The circuitry may be configured to transmit the location data entered by the caregiver and a bed identification (ID) from the bed. The circuitry may be configured to play a voice prompt to remind the caregiver to manually enter the location data after a threshold period of time may have elapsed subsequent to a power plug of the circuitry being plugged into an alternating current (AC) outlet of the healthcare facility and subsequent to casters of the frame being braked.

In some embodiments of the second aspect, the circuitry also may command the GUI to display a first screen of at least one interface screen that may be used by the caregiver to manually enter location data after the threshold period of time may have elapsed. The location data may include a room number, for example. Optionally, the first screen appearing on the GUI may include a button that is selectable to initiate manual entry of the location data. If desired, a room menu screen may appear on the GUI in response to the button being selected on the first screen. The room menu screen may permit the caregiver to select a room number from a list of room numbers. Alternatively or additionally, a campus icon and a unit icon may appear on the GUI in response to the button being selected on the first screen. The campus icon may be selectable to cause a campus menu list to be displayed on the GUI and the unit icon may be selectable to cause a unit menu list to be displayed on the GUI.

Further according to the second aspect, the circuitry may include a wireless communication module that may be configured to wirelessly transmit the location data and the bed ID to a wireless access point for delivery to at least one remote computer for purposes of making a bed-to-room association. Optionally, the wireless communication module also may transmit bed status data from the bed.

In some embodiments of the second aspect, the GUI may include a change location button that may be selectable by the caregiver to initiate a change of the location data prior to the threshold period of time elapsing. A room menu screen may appear on the GUI in response to the change location button being selected. The room menu screen may permit the caregiver to select a room number from a list of room numbers. Alternatively or additionally, a campus icon and a unit icon may appear on the GUI in response to the change location button being selected. The campus icon may be selectable to cause a campus menu list to be displayed on the GUI and the unit icon may be selectable to cause a unit menu list to be displayed on the GUI.

According to a third aspect of the present disclosure, a method of manually associating a patient bed to a location in a healthcare facility may be provided. The method may include determining with circuitry of the patient bed that a power plug of the patient bed may be plugged into an alternating current (AC) outlet of the healthcare facility. The method may also include determining with the circuitry of the patient bed that casters of the patient bed may be braked. Subsequent to determining that the power plug may be plugged into the AC outlet and subsequent to determining that the casters may be braked, the method may further include determining with the circuitry of the patient bed whether a threshold period of time may have elapsed. After the threshold period of time may have elapsed, the method may include displaying on a graphical user interface (GUI) of the patient bed at least one user interface screen that may be configured to be used by a caregiver to manually enter location data that may be indicative of a location in the healthcare facility at which the patient bed may be located. The method further may include transmitting from the patient bed using the circuitry of the patient bed the location data entered by the caregiver and a bed identification (ID).

In some embodiments of the third aspect, the method further may include displaying on the GUI a change location button that may be selectable by the caregiver to initiate a change of the location data prior to the threshold period of time elapsing. Optionally, in response to selection of the change location button by the caregiver, the method may include displaying a room menu screen on the GUI. The room menu screen may be configured to permit the caregiver to select a room number from a list of room numbers. Alternatively or additionally, in response to selection of the change location button by the caregiver, the method may include displaying a campus icon and a unit icon on the GUI. The campus icon may be selectable to cause a campus menu list to be displayed on the GUI and the unit icon may be selectable to cause a unit menu list to be displayed on the GUI.

Further according to the third aspect, displaying on the graphical user interface (GUI) of the patient bed at least one user interface screen may include displaying a first screen. The first screen may appear on the GUI after the threshold period of time may have elapsed and may include a button that may be selectable to initiate manual entry of the location data. The button on the first screen is different than the change location button mentioned above. The method of the third aspect may further include, in response to selection of the button by the caregiver on the first screen, displaying a room menu screen on the GUI. The room menu screen may be configured to permit the caregiver to select a room number from a list of room numbers. Alternatively or additionally, in response to selection of the button by the caregiver on the first screen, the method of the third aspect may include displaying a campus icon and a unit icon on the GUI. The campus icon may be selectable to cause a campus menu list to be displayed on the GUI and the unit icon may be selectable to cause a unit menu list to be displayed on the GUI.

If desired, transmitting from the patient bed using the circuitry of the patient bed the location data entered by the caregiver and the bed ID may include using a wireless communication module to wirelessly transmit the location data and the bed ID to a wireless access point for delivery to at least one remote computer for purposes of making a bed-to-room association. Optionally, the method of the third aspect may further include using the wireless communication module to wirelessly transmit bed status data from the bed. Further optionally, the method of the third aspect may include playing a voice prompt using the circuitry of the patient bed to remind the caregiver to manually enter the location data after the threshold period of time may have elapsed.

According to a fourth aspect of the present disclosure, a method of manually associating a patient bed to a location in a healthcare facility may be provided. The method may include determining with circuitry of the patient bed that a power plug of the patient bed may be plugged into an alternating current (AC) outlet of the healthcare facility. The method may also include determining with the circuitry of the patient bed that casters of the patient bed may be braked. Subsequent to determining that the power plug may be plugged into the AC outlet and subsequent to determining that the casters may be braked, the method may further include determining with the circuitry of the patient bed whether a threshold period of time may have elapsed. After the threshold period of time may have elapsed, the method may include using the circuitry to play a voice prompt to remind a caregiver to manually enter location data using a graphical user interface (GUI) of the patient bed that may display at least one user interface screen configured to be used by the caregiver to manually enter the location data that may be indicative of a location in the healthcare facility at which the patient bed may be located. The method further may include transmitting from the patient bed using the circuitry of the patient bed the location data entered by the caregiver and a bed identification (ID).

In some embodiments of the fourth aspect, the at least one user interface screen may include a first screen and the method may include displaying on the first screen a button that may be selectable to initiate manual entry of the location data. If desired, in response to selection of the button by the caregiver on the first screen, the method may include displaying a room menu screen on the GUI. The room menu screen may be configured to permit the caregiver to select a room number from a list of room numbers. Alternatively or additionally, in response to selection of the button by the caregiver on the first screen, the method of the fourth aspect may include displaying a campus icon and a unit icon on the GUI. The campus icon being selectable to cause a campus menu list to be displayed on the GUI and the unit icon may be selectable to cause a unit menu list to be displayed on the GUI.

If desired, transmitting from the patient bed using the circuitry of the patient bed the location data entered by the caregiver and the bed ID may include using a wireless communication module to wirelessly transmit the location data and the bed ID to a wireless access point for delivery to at least one remote computer for purposes of making a bed-to-room association. Optionally, the method of the fourth aspect may further include using the wireless communication module to wirelessly transmit bed status data from the bed.

Further according to the fourth aspect, the method may include displaying on the GUI a change location button that may be selectable by the caregiver to initiate a change of the location data prior to the threshold period of time elapsing. Optionally, in response to selection of the change location button by the caregiver, the method may include displaying a room menu screen on the GUI. The room menu screen may be configured to permit the caregiver to select a room number from a list of room numbers. Alternatively or additionally, in response to selection of the change location button by the caregiver, the method may include displaying a campus icon and a unit icon on the GUI. The campus icon may be selectable to cause a campus menu list to be displayed on the GUI and the unit icon may be selectable to cause a unit menu list to be displayed on the GUI.

According to a fifth aspect of the disclosed embodiments, a patient bed may include a frame configured to support a patient. Circuitry may be carried by the frame. A graphical user interface (GUI) may be carried by the frame and coupled to the circuitry. The graphical user interface may display at least one user interface screen that is used by a caregiver to manually validate patient identification data indicative of a identification of a patient positioned on the patient bed. The circuitry may be configured to transmit the patient identification data validated by the caregiver and a bed identification (ID) from the bed. The circuitry may command the GUI to display a first screen of the at least one interface screen that is used by the caregiver to validate the patient identification data. The circuitry may command the GUI to display a second screen of the at least one interface screen that displays a patient validation icon indicative of whether the patient identification data has been validated.

In some embodiments of the fifth aspect, a weigh scale may be configured to output a signal to the circuitry indicative of a weight of the patient. The circuitry may command the GUI to display a third screen displaying the weight of the patient. The third screen may include a save icon. Selection of the save icon may cause the circuitry to transmit data indicative of the weight of the patient and the validated patient identification data to an electronic medical record if the patient identification data has been validated. Selection of the save icon may cause the circuitry to transmit the data indicative of the weight of the patient and invalidated patient identification data to an electronic medical record if the patient identification data has not been validated.

If desired, in the fifth aspect, the circuitry may be configured to prompt the caregiver to manually enter location data of the patient bed after a threshold period of time elapses subsequent to a power plug of the circuitry being plugged into an outlet of a healthcare facility and subsequent to casters of the frame being braked. The location data may include a room number of the healthcare facility.

Optionally, in the fifth aspect, the validation icon may be illuminated in a first color in response to the patient identification data being validated. The validation icon may be illuminated in a second color that is different from the first color in response to the patient identification data not being validated. The second screen of the at least one interface screen may display a name of the patient in response to the patient identification data being validated.

Further, in the fifth aspect, the patient identification data may be temporarily invalidated in response to the circuitry being unplugged from an outlet of a healthcare facility. The patient identification data may be temporarily invalidated in response to the patient exiting the bed. The patient identification data may be invalidated in response to the patient bed being moved within a healthcare facility. The patient identification data may be invalidated in response to a new patient being positioned on the patient bed.

It may be contemplated that, in the fifth aspect, the first screen appearing on the GUI after the threshold period of time elapses includes a button that is selectable to initiate manual validation of the patient identification data. The circuitry may include a wireless communication module configured to wirelessly transmit the patient identification data to a wireless access point for delivery to at least one remote computer for purposes of making a bed-to-patient association. The wireless communication module may be configured to transmit bed status data from the bed. The circuitry may be configured to play a voice prompt to remind the caregiver to manually validate the patient identification data after the threshold period of time elapses.

According to a sixth aspect of the disclosed embodiments, a patient bed may include a frame configured to support a patient. Circuitry may be carried by the frame. A graphical user interface (GUI) may be carried by the frame and coupled to the circuitry. The graphical user interface may display at least one user interface screen that is used by a caregiver to manually validate patient identification data indicative of a patient positioned on the patient bed. The circuitry may be configured to transmit the patient identification data validated by the caregiver and a bed identification (ID) from the bed. The circuitry may command the GUI to display a first screen of the at least one interface screen that is used by the caregiver to validate the patient identification data. The circuitry may command the GUI to display a second screen of the at least one interface screen that displays a patient validation icon indicative of whether the patient identification data has been validated. A weigh scale may be configured to output a signal to the circuitry indicative of a weight of the patient. The circuitry may command the GUI to display a third screen displaying the weight of the patient. The circuitry may be configured to prompt the caregiver to manually enter a location data of the patient bed. The location data may be indicative of a location of the patient bed in a healthcare facility.

In some embodiments of the sixth aspect, the third screen may include a save icon. Selection of the save icon may cause the circuitry to transmit data indicative of the weight of the patient and the validated patient identification data to an electronic medical record if the patient identification data has been validated. Selection of the save icon may cause the circuitry to transmit the data indicative of the weight of the patient and invalidated patient identification data to an electronic medical record if the patient identification data has not been validated. The location data may include a room number of the healthcare facility.

Optionally, in the sixth aspect, the validation icon may be illuminated in a first color in response to the patient identification data beingt validated. The validation icon may be illuminated in a second color that is different from the first color in response to the patient identification data not being validated.

If desired, in the sixth aspect, the second screen of the at least one interface screen may display a name of the patient in response to the patient identification data being validated. The patient identification data may be temporarily invalidated in response to at least one of the circuitry being unplugged from an outlet of the healthcare facility or the patient exiting the bed. The patient identification data may be invalidated in response to at least one of the patient bed being moved within the healthcare facility or a new patient being positioned on the patient bed.

Additional features, which alone or in combination with any other feature(s), such as those listed above and/or those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which.

DETAILED DESCRIPTION

Figure 1:
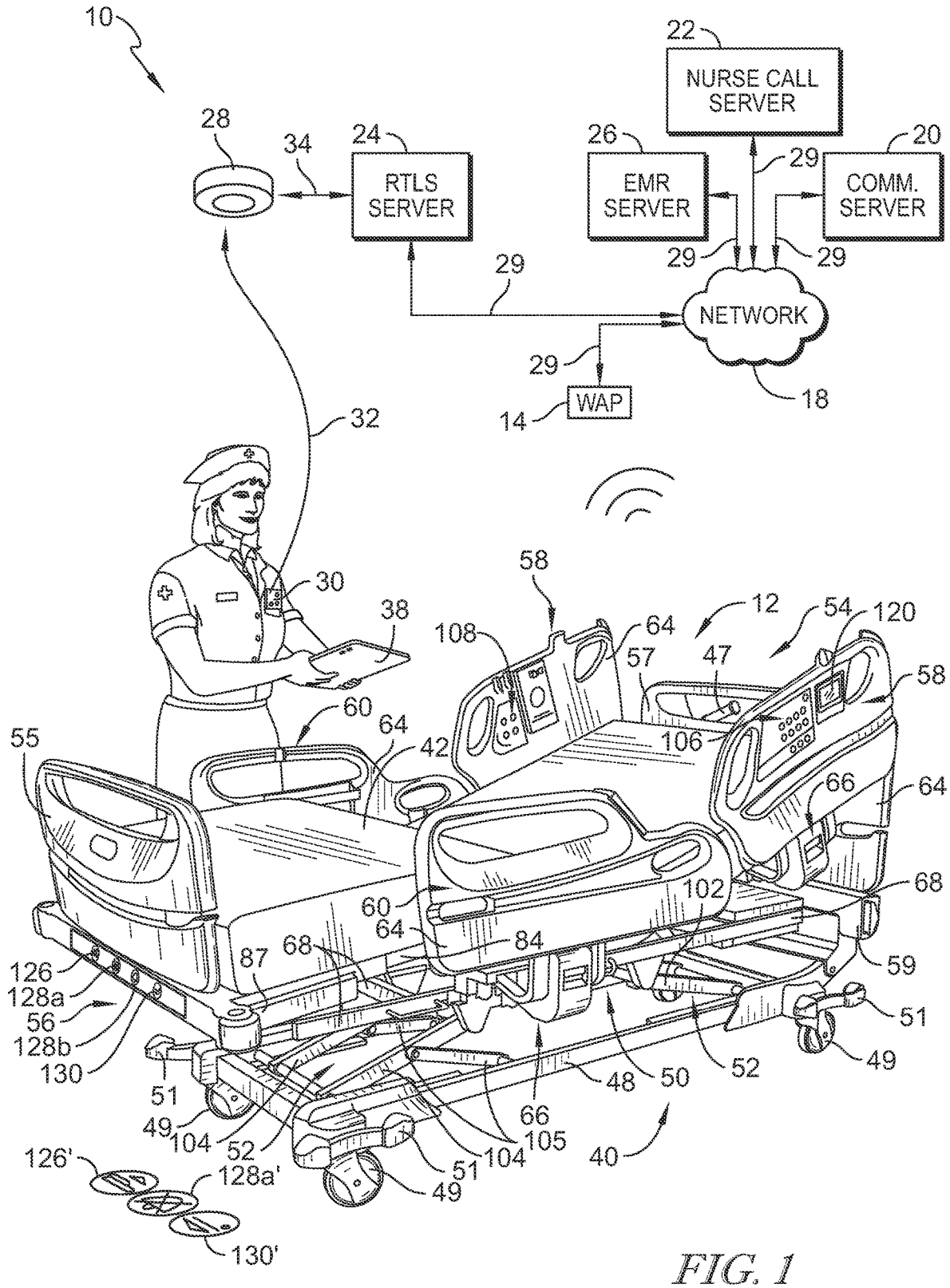
FIG. 1 is a diagrammatic view of a bed manual locating system showing a patient bed wirelessly coupled to a network via a wireless access point for communication with a real time locating system (RTLS) server, an electronic medical record (EMR) server, and a communications server.
Figure 2:
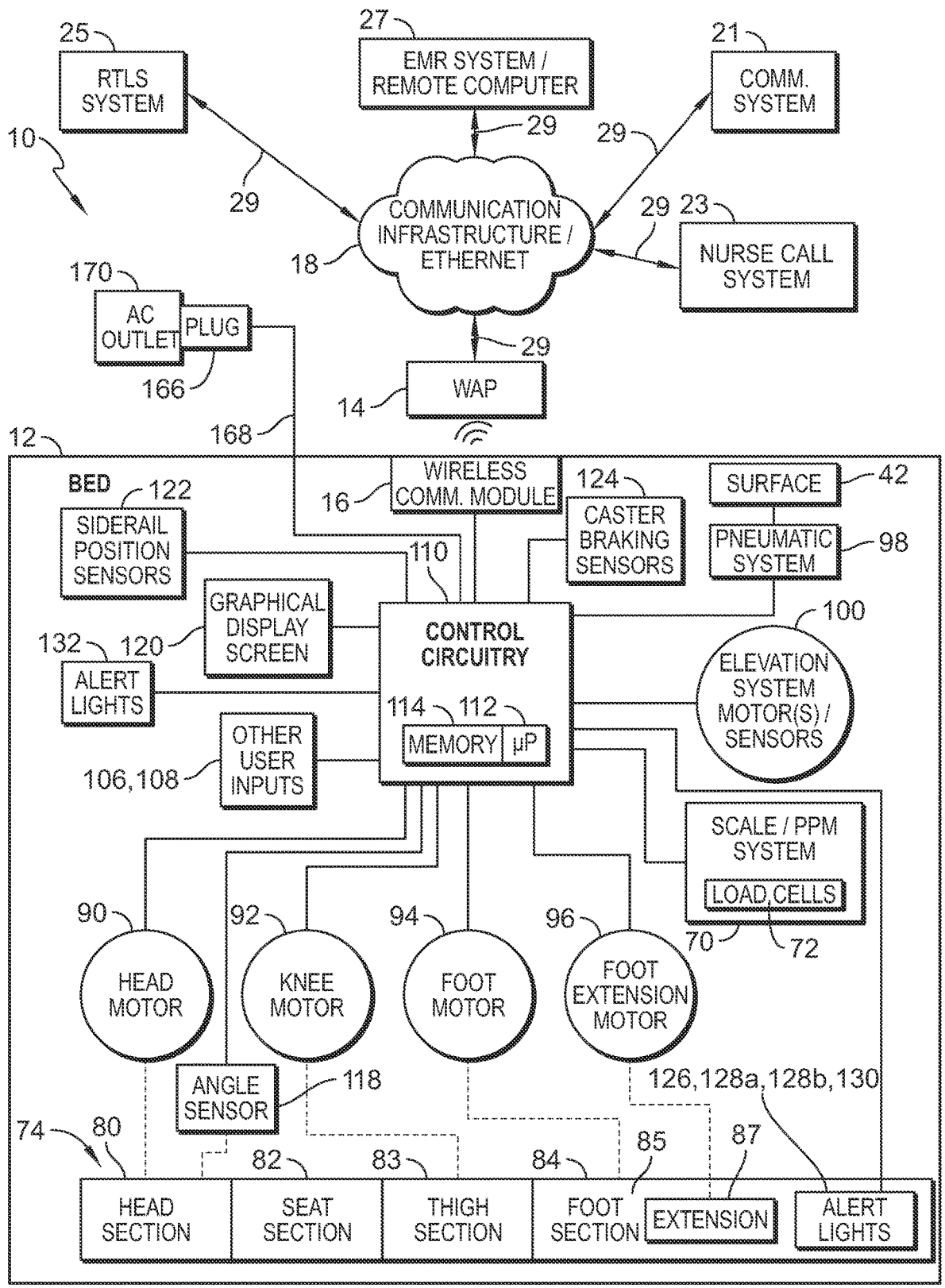
FIG. 2 is a block diagram showing various components of the patient bed of FIG. 1 and also showing the RTLS, EMR, nurse call, and communications systems of the network.

A bed manual locating system 10 includes a plurality of patient beds 12, only one of which is shown in FIG. 1, coupled to a network 18 of a healthcare facility such as a hospital, outpatient care facility, nursing home, and the like. In the illustrative example, patient bed 12 is coupled to network 18 via a wireless access point (WAP) 14 which may or may not be located in the respective patient room with the bed 12. It should be understood that, although only one WAP 14 is shown in FIG. 1, multiple WAP's 14 may be in wireless communication with bed 12. Illustratively, bed 12 includes a wireless communication module 16, as shown in FIG. 2, that sends wireless signals, such as radio frequency (RF) signals, or transmissions to WAP 14 and that receives wireless signals, such as RF signals, or transmissions from WAP. Thus, wireless communication module 16 includes a transceiver in some embodiments.

As shown diagrammatically in FIGS. 1 and 2, a communication server 20 of a corresponding communication system 21, a nurse call server 22 of a corresponding nurse call system 23, a real time locating system (RLTS) server 24 of a corresponding RTLS 25, and an electronic medical records (EMR) server 26 of an EMR system 27 are each coupled to network 18. Block 27 also is intended to represent other remote computers of network 18 that are included in system 10 in lieu of or in addition to depicted servers 20, 22, 24, 26. For example, system 10 includes an admission/discharge/transfer (ADT) server and/or a bed status data server in some embodiments. Double headed arrows 29 in FIGS. 1 and 2 represent the bidirectional communication links between network 18, WAP 14 (and the corresponding bed 12) and each of servers 20, 22, 24, 27 of respective systems 21, 23, 25, 27 and therefore, with each other. Communication links 29 include wired communication links or wireless communication links or both at the option of the designer of system 10 in any given healthcare facility. The wireless communication between the WAP's 14 of network 18 and module 16 of bed 12 contemplated by this disclosure includes Bluetooth (BT), Bluetooth Low Energy (BLE), Zigbee, Z-Wave, and WiFi (e.g., any of the 802.11$_x$ protocols). However, this is not rule out other types of wireless communication between bed 12 and an appropriately configured transceiver in addition to or in lieu of WAP 14, including infrared (IR) communications, ultrasonic (US) communications, ultra-wideband (UWB) communications, and so forth.

The RTLS 25 of system 10 includes wireless transceiver units 28 placed throughout the healthcare facility. Only one such unit 28 is depicted diagrammatically in FIG. 1. The RTLS 25 of system 10 also includes caregiver locating or tracking tags or badges 30 that are worn by caregivers. Each of the transceiver units 28 receives a wireless signal from the badges 30 of each of the caregivers wearing badges 30 and that are within communication range of the respective unit 28 as indicated diagrammatically by arrow 32 in FIG. 1. The wireless signal from each badge 30 includes badge identification data (ID) which is unique to the corresponding badge 30. Unit 28 then transmits its ID, which corresponds to a particular location in the healthcare facility, and the badge (ID) to RTLS server 24 as indicated diagrammatically by a bidirectional communication link 34 in FIG. 1. Based on the received badge ID and the location ID from unit 28, server 24 determines the location of the caregiver within the healthcare facility. Some healthcare facilities do not include RTLS 25 in which case server 24, transceivers 28, and badges 30 are omitted from system 10.

In some embodiments, RTLS server 24 is included in system 10 and transceivers 28 and badges 30 are omitted. In such embodiments, RTLS server 24 serves as a data repository for bed-to-room associations that are established via manual entry at beds 12 as will be discussed in further detail below in connection with FIGS. 3, 4A and 4B. Alternatively, the bed-to-room associations established via manual entry at beds 12 are stored in another server, such as nurse call server 22, EMR server, or any other server of system 10, including severs 20. Thus, servers 20, 22, 26, or other servers of system 10, may serve multiple purposes and so these may be configured to serve the RTLS function along with their other function(s) (e.g., nurse call, EMR, communications, etc.).

Figure 3:
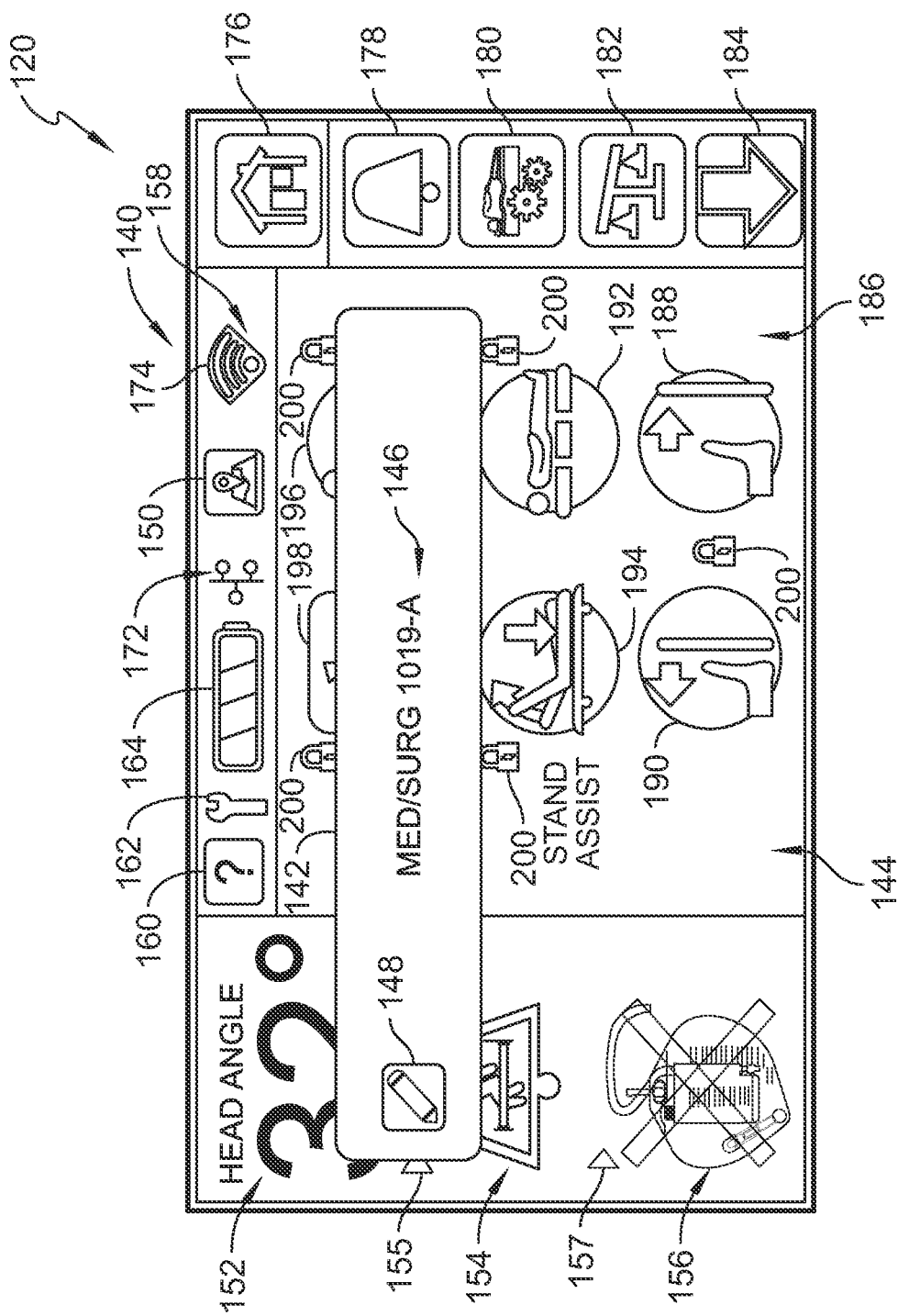
FIG. 3 is a diagrammatic view showing a graphical user interface (GUI) of the patient bed having a touch screen display that displays a window having a room number and an edit icon or button.
Figure 4A:
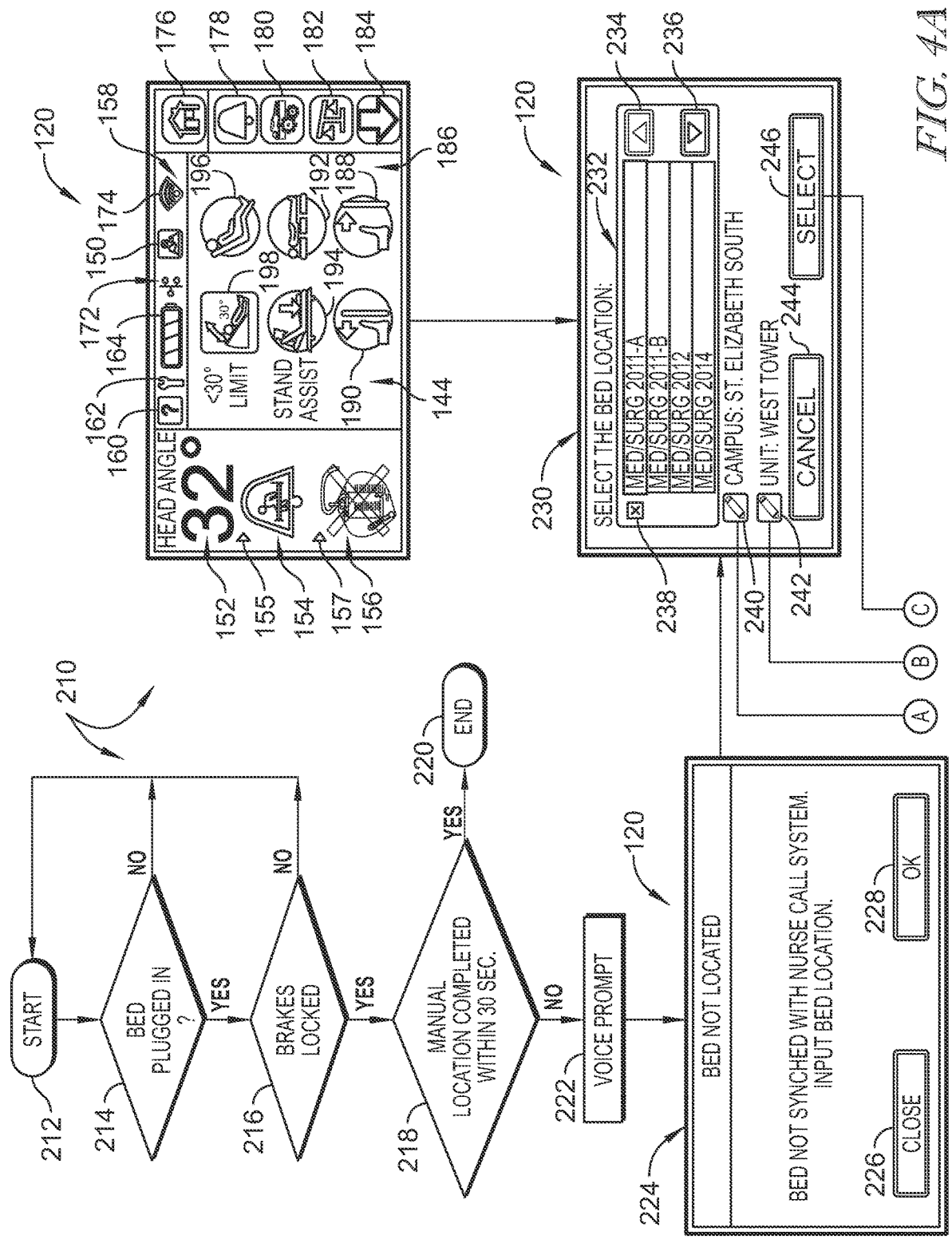
FIGS. 4A and 4B together make up a diagrammatic view having a flow chart portion in FIG. 4A and having screen flows showing how the GUI of the bed is used to manually enter location data for the patient bed.
Figure 4B:
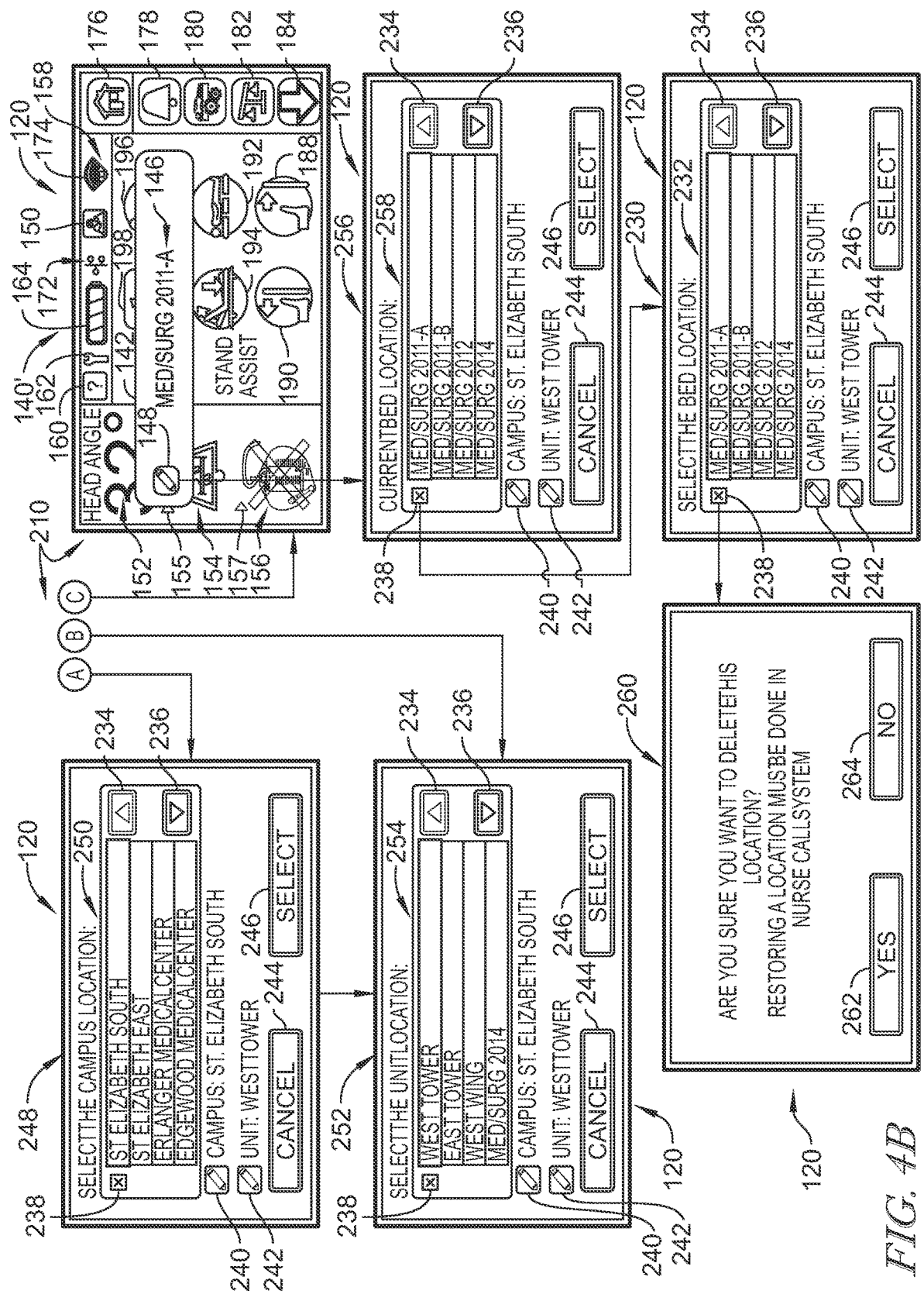

In some embodiments having RTLS 25 with transceivers 28 and tags 30 to track caregiver locations, the location of assets such as beds 12 can also be tracked in a similar manner by server 24 by attaching asset tags that are substantially the same as badges 30 to the assets to be tracked. However, in such systems 10 in which beds 12 have asset tags for tracking by RTLS 25, then manual association of beds 12 to rooms as discussed below in connection with FIGS. 3, 4A and 4B is not needed. However, hybrid systems 10 in which some locations of beds 12 are determined by signals from respective asset tags attached to the beds 12 and in which some locations of beds 12 are determined by manual entry at the respective beds 12, are contemplated by the present disclosure. In FIG. 1, the caregiver is shown carrying a tablet computer 38 which is configured to communicate wirelessly with other devices of network 18 such as via communications server 20. Mobile phones are carried by caregivers in addition to, or in lieu of tablet computers 38, and are in communication with communication server 20 in some embodiments.

As alluded to above, the present disclosure is primarily focused on manual entry of locating information at beds 12. However, a discussion is provided below of the basic components and operation of various features of bed 12 so that an understanding of the types of bed status data transmitted wirelessly by module 16 to WAP 14 can be gained. From the below discussion it will be appreciate that beds 12 having capability for manual entry of location information are by themselves, or in combination with the other components of system 10, a practical application of the concepts and ideas disclosed herein. Bed 12 includes a patient support structure such as a frame 40 that supports a surface or mattress 42 as shown in FIG. 1. It should be understood that FIG. 1 shows some details of one possible bed 12 having one specific configuration. In particular, illustrative bed 12 of FIG. 1 is the CENTRELLA® bed available from Hill-Rom Company, Inc. Other aspects of illustrative bed 12 are shown and described in more detail in U.S. Patent Application Publication No. 2018/0161225 A1 which is hereby expressly incorporated by reference herein to the extent not inconsistent with the present disclosure which shall control as to any inconsistencies. However, this disclosure is applicable to other types of patient support apparatuses 12 having other configurations, including other types of beds, surgical tables, examination tables, stretchers, chairs, wheelchairs, patient lifts and the like.

Still referring to FIG. 1, frame 40 of bed 12 includes a base frame 48 (sometimes just referred herein to as a base 48), an upper frame assembly 50 and a lift system 52 coupling upper frame assembly 50 to base 48. Lift system 52 is operable to raise, lower, and tilt upper frame assembly 50 relative to base 48. Bed 12 has a head end 54 and a foot end 56. Patient bed 12 further includes a footboard 55 at the foot end 56 and a headboard 57 at the head end 54. Illustrative bed 12 includes a pair of push handles 47 coupled to an upstanding portion 59 of base 48 at the head end 54 of bed 12. Only a portion of one push handle 47 can be seen in FIG. 1. Headboard 57 is coupled to upstanding portion 59 of base as well. Footboard 55 is coupled to upper frame assembly 50. Base 48 includes wheels or casters 49 that roll along floor (not shown) as bed 12 is moved from one location to another. A set of foot pedals 51 are coupled to base 48 and are used to brake and release casters 49.

Illustrative patient bed 12 has four siderail assemblies coupled to upper frame assembly 50 as shown in FIG. 1. The four siderail assemblies include a pair of head siderail assemblies 58 (sometimes referred to as head rails) and a pair of foot siderail assemblies 60 (sometimes referred to as foot rails). Each of the siderail assemblies 58 and 60 is movable between a raised position, as shown in FIG. 1, and a lowered position (not shown). Siderail assemblies 58, 60 are sometimes referred to herein as siderails 58, 60. Each siderail 58, 60 includes a barrier panel 64 and a linkage 66. Each linkage 66 is coupled to the upper frame assembly 50 and is configured to guide the barrier panel 64 during movement of siderails 58, 60 between the respective raised and lowered positions. Barrier panel 64 is maintained by the linkage 66 in a substantially vertical orientation during movement of siderails 58, 60 between the respective raised and lowered positions.

Upper frame assembly 50 includes various frame elements 68, shown in FIG. 1, that form, for example, a lift frame and a weigh frame supported with respect to the lift frame by a set of load cells 72 of a scale and/or bed exit/patient position monitoring (PPM) system 70 of bed 12, as shown diagrammatically in FIG. 2. A patient support deck 74, shown diagrammatically in FIG. 2, is carried by the weigh frame portion of upper frame assembly 50 and supports mattress 42 thereon. Data relating to the operation of the scale and/or bed exit/PPM system 70 is among the features of bed 12 for which bed status data is transmitted wirelessly from module 16 to one or more WAP's 14.

Patient support deck 74 includes a head section 80, a seat section 82, a thigh section 83 and a foot section 84 in the illustrative example as shown diagrammatically in FIG. 2. Sections 80, 83, 84 are each movable relative to the weigh frame portion of upper frame assembly 50. For example, head section 80 pivotably raises and lowers relative to seat section 82 whereas foot section 84 pivotably raises and lowers relative to thigh section 83. Additionally, thigh section 83 articulates relative to seat section 82. Also, in some embodiments, foot section 84 is extendable and retractable to change the overall length of foot section 84 and therefore, to change the overall length of deck 74. For example, foot section 84 includes a main portion 85 and an extension 87 in some embodiments as shown diagrammatically in FIG. 2.

In the illustrative embodiment, seat section 82 is fixed in position with respect to the weigh frame portion of upper frame assembly 50 as patient support deck 74 moves between its various patient supporting positions including a horizontal position to support the patient in a supine position, for example, and a chair position (not shown) to support the patient in a sitting up position. In other embodiments, seat section 82 also moves relative to upper frame assembly 50, such as by pivoting and/or translating. Of course, in those embodiments in which seat section 82 translates relative to the upper frame assembly 50, the thigh and foot sections 83, 84 also translate along with seat section 82. As bed 12 moves from the horizontal position to the chair position, foot section 84 lowers relative to thigh section 83 and shortens in length due to retraction of the extension 87 relative to main portion 85. As bed 12 moves from the chair position to the horizontal position, foot section 84 raises relative to thigh section 83 and increases in length due to extension of the extension 87 relative to main portion 85. Thus, in the chair position, head section 80 extends upwardly from upper frame assembly 50 and foot section 84 extends downwardly from thigh section 83.

As shown diagrammatically in FIG. 2, bed 12 includes a head motor or actuator 90 coupled to head section 80, a knee motor or actuator 92 coupled to thigh section 83, a foot motor or actuator 94 coupled to foot section 84, and a foot extension motor or actuator 96 coupled to foot extension 87. Motors 90, 92, 94, 96 may include, for example, an electric motor of a linear actuator. In those embodiments in which seat section 82 translates along upper frame assembly 50 as mentioned above, a seat motor or actuator (not shown) is also provided. Head motor 90 is operable to raise and lower head section 80, knee motor 92 is operable to articulate thigh section 83 relative to seat section 82, foot motor 94 is operable to raise and lower foot section 84 relative to thigh section 83, and foot extension motor 96 is operable to extend and retract extension 87 of foot section 84 relative to main portion 85 of foot section 84. Data relating to the operation of motors 90, 92, 94, 96 and the positions of deck sections 80, 82, 83, 84 is among the features of bed 12 for which bed status data is transmitted wirelessly from module 16 to one or more WAP's 14.

In some embodiments, bed 12 includes a pneumatic system 98 that controls inflation and deflation of various air bladders or cells of mattress 42. The pneumatic system 98 is represented in FIG. 2 as a single block but that block 98 is intended to represent one or more air sources (e.g., a fan, a blower, a compressor) and associated valves, manifolds, air passages, air lines or tubes, pressure sensors, and the like, as well as the associated electric circuitry, that are typically included in a pneumatic system for inflating and deflating air bladders of mattresses. Operation of pneumatic system 98 is among the features of bed 12 for which bed status data is transmitted wirelessly from module 16 to one or more WAP's 14.

As also shown diagrammatically in FIG. 2, lift system 52 of bed 12 includes one or more elevation system motors or actuators 100, which in some embodiments, comprise linear actuators with electric motors. Thus, actuators 100 are sometimes referred to herein as motors 100 and operation of the motors 100 is among the features of bed 12 for which bed status data is transmitted wirelessly from module 16 to one or more WAP's. Alternative actuators or motors contemplated by this disclosure include hydraulic cylinders and pneumatic cylinders, for example. The motors 100 of lift system 52 are operable to raise, lower, and tilt upper frame assembly 50 relative to base 48. In the illustrative embodiment, one of motors 100 is coupled to, and acts upon, a set of head end lift arms 102 and another of motors 100 is coupled to, and acts upon, a set of foot end lift arms 104 to accomplish the raising, lowering and tilting functions of upper frame 50 relative to base 48. Guide links 105 are coupled to base 48 and to lift arms 104 in the illustrative example as shown in FIG. 1.

Each of siderails 58 includes a first user control panel 106 coupled to the outward side of the associated barrier panel 64. Controls panels 106 include various buttons that are used by a caregiver to control associated functions of bed 12. For example, control panel 106 includes buttons that are used to operate head motor 90 to raise and lower the head section 80, buttons that are used to operate knee motor 92 to raise and lower the thigh section 83, and buttons that are used to operate motors 100 to raise, lower, and tilt upper frame assembly 50 relative to base 48. In some embodiments, control panel 106 also includes buttons that are used to operate motor 94 to raise and lower foot section 84 and buttons that are used to operate motor 96 to extend and retract foot extension 87 relative to main portion 85. Each of siderails 58 also includes a second user control panel 108 coupled to the inward side of the associated barrier panel 64. Controls panels 108 include various buttons that are used by a patient to control associated functions of bed 12. In some embodiments, the buttons of control panels 106, 108 comprise membrane switches that are used to control head motor 90 and knee motor 92.

As shown diagrammatically in FIG. 2, bed 12 includes control circuitry 110 that is electrically coupled to motors 90, 92, 94, 96 and to motors 100 of lift system 52. Control circuitry 110 is sometimes referred to as a "controller." Control circuitry 110 is represented diagrammatically as a single block in FIG. 2, but control circuitry 110 in some embodiments, comprises various circuit boards, electronics modules, and the like that are electrically and communicatively interconnected. Control circuitry 110 includes one or more microprocessors 112 or microcontrollers that execute software to perform the various control functions and algorithms described herein. Thus, circuitry 110 also includes memory 114 for storing software, variables, calculated values, and the like as is well known in the art. Memory 112 comprises, for example, one or more flash memory banks such as one or more EEPROM's, EPROM's, and the like. In some embodiments, memory 112 is included on the same integrated circuit chip as microprocessor 112.

As shown diagrammatically in FIG. 2, an "other user inputs" block represents the various user inputs such as buttons of control panels 106, 108, for example, that are used by the caregiver or patient to communicate input signals to control circuitry 110 of bed 12 to command the operation of the various motors 90, 92, 94, 96, 100 of bed 12, as well as commanding the operation of other functions of bed 12. Bed 12 includes at least one graphical user input (GUI) or display screen 120 coupled to a respective siderail 58 as shown in FIG. 1. Display screen 120 is coupled to control circuitry 110 as shown diagrammatically in FIG. 2. In some embodiments, two graphical user interfaces 120 are provided and are coupled to respective siderails 58. Alternatively or additionally, one or more graphical user interfaces are coupled to siderails 60 and/or to one or both of the headboard 57 and footboard 55 or some other portion of bed 12 such as a support arm assembly extending upwardly from base frame 48 or upper frame 50.

Still referring to FIG. 2, wireless communication module 16 is also coupled electrically to control circuitry 110 and is configured for wireless communication with network 18 and its associated devices without the use of any wired bed cable in the illustrative embodiment. The communication of data from module 16 is among the features of bed 12 controlled by the bed operating software of control circuitry 110.

Still referring to FIG. 2, bed 12 includes various sensors to sense the states or positions of various portions of bed 12. In the illustrative example, bed 12 includes an angle sensor 118 coupled to head section 80 to sense an angle of head section elevation (sometimes referred to as the head-of-bed (HOB) angle). Angle sensor 118 includes an accelerometer (single-axis or multi-axis) in some embodiments. In such embodiments, the HOB angle is measured with respect to a horizontal reference axis and/or with respect to a vertical reference axis depending upon the orientation of the accelerometer relative to head section 80 and depending upon the type of accelerometer used. In other embodiments, angle sensor 118 includes a rotary potentiometer which measures the HOB angle between head section 90 and another portion of frame 40 such as one of frame members 68 of upper frame assembly 50. In further embodiments, angle sensor 118 is included in head motor 90 and has an output that correlates to the HOB angle. Motor 90 may include, for example, a shaft encoder, a Hall effect sensor, a rotary potentiometer, or some other sensor which serves as angle sensor 118 of bed 12 in such embodiments. Similar such sensors are included in elevation system motors 100 in some embodiments and are used to determine the position of upper frame assembly 50 relative to base 48 such as the height of upper frame assembly 50 and/or amount of tilt of upper frame assembly 50 relative to base 48.

Bed 12 also includes siderail position sensors 122 to sense the position (e.g., raised and/or lowered) of each of siderails 58, 60 and one or more caster braking sensors 124 to sense whether casters 49 are braked or released. In some embodiments, sensors 122, 124 include limit switches that are engaged or disengaged by a linkage mechanism, such as linkage 66 in the case of siderails 58, 60, to produce output signals indicative of the position of the respective mechanical structure. Alternatively, Hall effect sensors may be used as some or all of sensors 122, 124 in some embodiments. The foregoing types of sensors 122, 124 are just a couple examples of suitable sensors and therefore, this disclosure is intended to cover all types of sensors that may be used as sensors 122, 124. Each of the sensors mentioned above, including sensors internal to motors 100 and sensors 118, 122, 124 are each coupled electrical to control circuitry 110 for analysis and/or processing. Thus, data from sensors 118, 122, 124 is used by the bed operating software in connection with the control and operation of various features of bed 12 and is among the features of bed 12 for which bed status data is transmitted wirelessly from module 16 to one or more WAP's 14.

As shown in FIG. 1, bed 12 includes four status or alert lights 126, 128a, 128b, 130 at foot end 56 corresponding to various monitored features of bed 12. In the illustrative embodiment, for example, bed 12 includes a siderail position light 126, a bed exit/PPM disabled light 128a, a bed exit/PPM enabled light 128b, and a bed lowest position light 130. PPM is an acronym for "patient position monitoring." Alert lights 126, 128a, 128b, 130 are coupled to a lateral frame member of extension 87 of foot section 84 and are situated beneath footboard 55. In other embodiments, alert lights 126, 128a, 128b, 130 may be located elsewhere on bed 12 such as on base 48 and/or one or more of siderails 58, 60. In FIG. 2, alert lights 126, 128a, 128b, 130 are represented diagrammatically as a single block and are coupled electrically to control circuitry 110 to control the manner in which alert lights 126, 128a, 128b, 130 are illuminated as will be discussed in further detail below. In some embodiments, other alert lights 132, shown diagrammatically as a single block in FIG. 2, are located elsewhere on bed 12, such as on siderails 58, 60, and are illuminated to convey information regarding other features of bed 12, such as to indicate motor lockout conditions, alarm volume control levels, nurse call status, caster brake status, and the like.

In some embodiments, alert lights 126, 128b, 130 are illuminated different colors to indicate certain statuses. For example, lights 126, 128b, 130 are illuminated a first color, such as green for example, if the associated bed condition is in an acceptable or statifcatory state. Lights 126, 128b, 130 are illuminated a second color, such as amber or yellow for example, if the associated bed condition is an undesirable or unsatisfactory state. Each of lights 126, 128a, 128b, 130 has an icon on the lens of the respective light 126, 128a, 128b, 130 corresponding to the monitored condition of bed 12.

In the illustrative example, if bed 12 has a falls risk protocol enabled (i.e., turned on) in which all of siderails 58, 60 are required to be raised (or a subset of siderails 58, 60 selected on GUI 120 is required to be raised), the light 126 is illuminated green if all of the siderails 58, 60 (or selected subset of siderails 58, 60) are in the respective raised positions (e.g., the desirable or satisfactory condition) and the light 126 is illuminated amber, and in some embodiments flashed, if any one or more of siderails 58, 60 (or selected subset of siderails 58, 60) is in the lowered position (e.g., the undesirable or unsatisfactory condition). In some embodiments, a lighted iconic image 126' corresponding to the state of light 126 is projected onto the floor at the foot end of the bed 12 as shown in FIG. 1. Image 126' has the same color and icon as light 126. If the falls risk protocol of bed 12 is disabled (i.e., turned off), then light 126 is turned off and no image 126' is projected onto the floor by bed 12.

If the bed exit/PPM system of bed 12 is disabled (i.e., turned off), then light 128a is illuminated blue and a corresponding blue lighted iconic image 128a' is projected onto the floor by bed 12. If the bed exit/PPM system of bed 12 is enabled (i.e., turned on), then light 128b is illuminated and a corresponding lighted iconic image (not shown) is projected onto the floor by bed 12 and appears in the same general location as image 128a'. Of course, when light 128b is illuminated, light 128a is turned off and image 128a' is no longer projected onto the floor. Light 128b and image 128b' are illuminated green when the bed exit/PPM system is armed (aka enabled) and the patient is on the bed in the proper location (e.g., the desirable or satisfactory condition). Some embodiments of bed 12 have multiple modes (e.g., patient movement, pre-exit, and exiting modes) with varying levels of sensitivities at which an alarm condition is considered to exist. Light 128b and image 128b' are illuminated amber, and in some embodiments are flashed, if the bed exit/PPM system is armed and the patient is not properly positioned on bed, including being out of bed altogether (e.g., the undesirable or unsatisfactory condition).

If bed 12 has the falls risk protocol enabled (i.e., turned on) control circuitry 110 monitors the position of the upper frame 50 relative to base frame 48 to assure that upper frame 50 is in its lowest position relative to base frame 48. If upper frame 50 is in its lowest position (e.g., the desirable or satisfactory condition), the light 130 is illuminated green (e.g., the desirable or satisfactory condition). On the other hand, if upper frame 50 is not in its lowest position (e.g., the undesirable or unsatisfactory condition), the light 130 is illuminated amber, and in some embodiments flashed. In some embodiments, a lighted iconic image 130' corresponding to the state of light 130 is projected onto the floor at the foot end of the bed 12 as shown in FIG. 1. Image 130' has the same color and icon as light 130. If the falls risk protocol of bed 12 is disabled (i.e., turned off), then light 130 is turned off and no image 130' is projected onto the floor by bed 12.

In some embodiments, an audible alarm of bed 12 may also sound under the control of control circuitry 110 if an unsatisfactory condition of a particular protocol or condition is detected. Lights 126, 128b, 130 are illuminated a third color if the associated protocol or condition is enabled for monitoring and at least one of the monitored bed statuses for the particular protocol or condition is undesirable (i.e., violated), but the associated alert has been suspended by the caregiver. If the alert has been suspended, any associated audible alarms may be turned off during the alarm suspension. A caregiver may suspend an alert associated with lights 126, 128b, 130, for example, when assisting a patient in getting out of bed 12 and going to the bathroom. The various alert conditions (aka alarm conditions) associated with the operation of alert lights 126, 128a, 126b, 130 and the audible alarms, if any, of bed 12 is among the features of bed 12 for which bed status data is transmitted wirelessly from module 16 to one or more WAP's 14.

Referring now to FIG. 3, a start-up screen 140 is shown on GUI 120. GUI 120 is embodied as a touch screen display having various icons or buttons that are selectable by a caregiver to navigate to other screens for selection of various bed functions and entry of various types of data as will be discussed below, primarily in connection with manual entry of bed location data on GUI 120. Start-up screen 140 appears on GUI, in some embodiments, in response to a caregiver (or really, any user for that matter) touching GUI 120 to wake GUI 120 from a dormant state in which GUI 120 is blacked out or, in some embodiments, in which GUI 120 displays a screen saver image of some sort.

Illustrative start-up screen 140 has a bed location window 142 superimposed over a home screen 144. Thus, FIG. 3 illustrates the situation in which a text string 146 of bed location information, illustratively "MED/SURG 1019-A," has been input manually during a previous use of GUI 120 by a caregiver. Window 142 includes an edit icon 148 that is selectable, such as by touching, to navigate to the screens that are used to edit the bed location information for whatever reason, such as if the bed 12 has been moved to a new room or if the hospital updates its room location naming convention. These edit screens are discussed below in connection with FIGS. 4A and 4B. Window 142 only appears over home screen 144 for a short period of time upon startup of GUI 120, such as on the order of 5 to 30 seconds, and then disappears such that only home screen 144 remains displayed on GUI 120. In some embodiments in which a healthcare facility is not equipped to receive information wirelessly from bed 12, then the manual location entry feature using GUI 120 is disabled. In such situations, window 142 does not appear over home screen 144 upon startup of the GUI 120.

Home screen 144 includes a location icon 150 that is color coded to indicate whether bed location information or data has been entered manually using GUI 120 or, in some embodiments, if bed location data is otherwise transmitted to bed 12 either wirelessly or via a wired cable such as if bed 12 has an asset tag for locating as discussed above and RTLS server 24 sends a message to bed 12 regarding its location or if RTLS system 25 is otherwise configured to accurately determine the location of bed 12 without the use of an asset tag (e.g., the bed 12 is coupled via a cable to an NIU, BIU, or ASBC having a location ID indicative of room location). In other words, bed 12 is configured to permit bed location information to be entered manually using GUI 120 and to receive bed location information from equipment external to bed 12, in some embodiments. In any event, if bed 12 has bed location information stored in memory 114 of control circuitry 110, then bed location icon 150 is color coded green in some embodiments. If bed 12 does not have any bed location information stored in memory 114, or if bed 12 has bed location information stored in memory 114 that is believed to be inaccurate based on sensed bed conditions such as unplugging of bed 12 from a wall outlet, unbraking or releasing of casters 49, and/or movement of bed to a new location, then bed location icon 150 is color coded yellow or amber in some embodiments.

For the sake of completeness, as shown in FIG. 3, other illustrative icons and information displayed on home screen 144 includes, along a left side of home screen 144, a head angle reading 152 corresponding to the HOB angle measured by angle sensor 118, a bed exit/PPM icon 154 indicating the mode in which the scale/PPM system 70 is operating when enabled, and a urinary drainage bag lockout icon 156 indicating whether a urinary drainage bag (aka a Foley bag) is coupled to a bracket (not shown) attached to foot section 84 of bed 12. A triangular edit button 155 is provided adjacent to icon 154 and is selectable to navigate to other screens for disabling the PPM system 70 of bed 12 or changing the mode in which the PPM system 70 operates. A similar triangular edit icon 157 is provided adjacent to icon 156 and is selectable to navigate to other screens for enabling and disabling the urinary drainage bag lockout feature of bed 12. In this regard, see U.S. Patent Application Publication No. 2018/0185222 A1 which is hereby incorporated by reference herein in its entirety to the extent not inconsistent with the present disclosure which shall control as to any inconsistencies.

Home screen 144 includes an upper field 158 in which bed location icon 150 is shown. Upper field 158 also includes a help icon 160 that is selectable to navigate to various help screens of bed 12, a service required icon 162 that is illuminated yellow or amber and flashes when bed service is needed, and a battery charge level indicator 164 having four segments that are illuminated green to indicate a battery charge level of a battery (not shown) of bed 12. However, when the battery charge gets low, the segment to the left of indicator 164 turns yellow and flashes. The battery of bed 12 is used to supply power to various components of bed 12 when a power plug 166 at the end of a power cable 168 of bed 12 (see FIG. 2) is unplugged from an alternating current (AC) outlet 170 of the healthcare facility.

Upper field 158 further includes a nurse call connectivity icon or indicator 172 that is color coded to indicate whether bed 12 is in communication with nurse call system 23 of the healthcare facility. In some embodiments, indicator 172 is color coded white when bed 12 is not in communication with nurse call system 23 which includes embodiments of system 10 in which nurse call system 23 is omitted altogether. In some embodiments, indicator is color coded green, such as by illuminating a green circle around the indicator 172 shown in FIG. 3. Finally, in the illustrative example, upper field 158 includes a WiFi connectivity icon or indicator 174 that is color coded to indicate whether wireless communication module 16 of bed 12 is communicating with one or more WAP's 14 and, in some embodiments, indicator 174 is a received signal strength indicator (RSSI) that indicates a relative level (e.g., low, medium, high) of the received signal strength of the wirless communication from the one or more WAP's received by module 16 of bed. In this regard, segments of indicator 174 are illuminated green when wireless communications exist between module 16 and at least one WAP 14 and indicator 174 is illuminated yellow or is not illuminated at all when no wireless communications exist between module 16 and WAP 14.

Still referring to FIG. 3, along a right side of home screen 144 a menu of icons are shown including a home button 176 that is selected to return to home screen 144 when viewing a screen on GUI other than home screen 144, an alerts button 178 that is pressed to navigate to other screens for controlling alerting functions of bed 12, a mattress control button 180 that is selected to navigate to other screens for controlling functions of mattress 42 and pneumatic system 98 of bed 12, a scale control button 182 that is selected to navigate to other screens for controlling functions of scale system 70 of bed 12, and a down arrow button 184 that is selected to cause other icons (aka buttons) to appear in the menu of icons at the right side of screen 144. After button 184 is selected, an up arrow button (similar to button 184 but with the arrow pointing upwardly instead of downwardly) appears at the top of the menu of icons. In other words, the down arrow button 184 and up arrow button, when present, provide scrolling functionality to the menu of icons of screen 144.

Home screen 144 further includes a central field 186 that includes various control icons or buttons for controlling functions of bed 12 as shown in FIG. 3. Field 186 includes a foot extension button 188 that is selected to operate foot extension motor 96 to extend extension 87 relative to main portion 85 to lengthen foot section 84. Field 186 also includes a foot retraction button 190 that is selected to operate motor 96 to retract extension 87 relative to main portion 85 to shorten foot section 84. Above button 188, field 186 includes a bed flat and level button 192 that operates one or more of motors 90, 92, 94, as needed, to move deck sections 80, 82, 83, 84 into a substantially flat or substantially coplanar orientation relative to each other and to operate one or more of the elevation system motors 100, as needed, to move the upper frame 50, and therefore the deck 74, into a substantially horizontal or substantially level orientation. The word "substantially" herein is intended to mean within plus or minus 10%, or less, of the desired condition and, at a minimum, within manufacturing tolerances of the desired condition. The movements of bed 12 associated with buttons 188, 190, 192 occur only while the respective buttons 188, 190, 192 are pressed or touched. Thus, if the caregiver disengages from any of buttons 188, 190, 192 the associated bed movement stops.

Field 186 further includes a stand assist button 194 situated above button 190 in the illustrative example. Button 194 is selected when a patient is sitting at a side of the mattress 42 of bed 12 and is getting ready to stand up from the bed. While button 194 is touched, motor 90 is operated as needed to move head section 80 to a raised position, motors 92, 94 are operated as needed to flatten or lower thigh and foot section 83, 84, motors 100 are operated as need to move the upper frame 50 to its low position relative to base frame 48, and if mattress 42 is an air mattress having its pneumatic system 98 controlled by control circuitry 110, to operate the pneumatic system 98 to increase the pressure in a seat section of the mattress 42. All of these motions and operations make it easier for the patient to sand up out of bed 12. For example, by raising the head section 80, the siderails 58 are moved into ergonomic positions for the patient grip while standing up.

Field 186 includes a chair button 196 situated above button 192. Button 196 is pressed to move deck 74, and therefore mattress 42 supported by deck 74 and the patient supported by the mattress 42, into a chair position. While button 196 is pressed, motor 90 is operated as needed to pivotably raise head section 80 relative to upper frame 50, motor 92 is operated as needed to pivotably raise thigh section 83 relative to upper frame 50, and motor 94 is operated as needed to pivotably lower foot section 94 relative to thigh section 83. Field 186 also includes a 30 degree limit control button 198 for enabling and disabling a 30 degree limit function of bed 12. When enabled, the 30 degree limit control prevents head section 80 of bed 12 from being lowered to a HOB angle less than 30 degrees. By keeping head section 80 raised above 30 degrees, some pulmonary complications such as ventilated assisted pneumonia (VAP) are inhibited from occurring. Sequential presses or touches of button 198 toggles the 30 degree limit function of bed 12 between enabled (i.e., on) and disabled (i.e., off) states.

Control panel 106 of bed 12 includes a master lockout button that, when pressed, permits any of buttons 188, 190, 192, 194, 196, 198 to be simultaneously pressed to lockout the associated function of buttons 188, 190, 192, 194, 196, 198. That is, when locked out, the respective button 188, 190, 192, 194, 196, cannot be used as an input to cause the associated bed movements. Also, when locked out, button 198 cannot be used to enable the 30 degree lockout function. In essence, when button 198 is locked out, the 30 degree limit function is locked in its disabled state. A lockout icon 200 is displayed in field 186 adjacent to the respective buttons 188, 190, 192, 194, 196, 198 that have been locked out. However, a single lockout icon 200 is shown to indicate that buttons 188, 190 related to foot section 84 extension and retraction are both been locked out together. After any of buttons 188, 190, 192, 194, 196, 198 are locked out, they are unlocked in the same manner as just described. That is, the master lockout button on control panel 106 is pressed and then the locked out button 188, 190, 192, 194, 196, 198 to be unlocked is pressed simultaneously. The master lockout button on panel 106 is a "hard" or analog button such as a membrane switch, for example, whereas the buttons of home screen 144 are "soft" buttons that are implemented in software as is known in the art.

Referring now to FIGS. 4A and 4B, a software algorithm 210 that is stored in memory 114 and executed by microprocessor 112 of control circuitry 110 of bed 12 is shown. Algorithm 210 includes the various steps, conditions, and user input selections that are implemented by bed 12 as a practical application for entering manual bed location data using GUI 120 of bed 12. Algorithm 210 starts at block 212 and proceeds to block 214 to determine whether bed 12 is plugged in. Thus, at block 214 control circuitry 110 determines whether plug 166 is connected to AC outlet 170 such that current or voltage is sensed by a power circuitry module (not shown) of control circuitry 110. The power circuitry module or circuitry 110 may include, for example, one or more transformers, rectifiers, voltage converters, voltage dividers, voltage regulators, resistors, inductors, capacitors, and the like, at the discretion of the bed designer.

If it is determined at block 214 of FIG. 4A that bed 12 is not plugged in, then algorithm 210 loops back to step 212 and proceeds from there. If it is determined at block 214 that bed 12 is plugged in, then algorithm 210 proceeds to block 216 where microprocessor 112 of control circuitry 110 determines whether casters 49 of bed 12 are braked or have their brakes locked against rolling based on signals from caster braking sensors 124. If it is determined at block 216 that casters 49 are not locked, then algorithm 210 loops back to step 212 and proceeds from there.

If it is determined at block 216 of FIG. 4A that casters 49 of bed 12 are braked or locked, then algorithm 210 proceeds to block 218 at which microprocessor 112 of control circuitry 110 determines whether manual location has been completed by a caregiver using GUI 120 within 30 seconds. Thus, microprocessor 112 implements a software timer for 30 seconds to give the caregiver time to manually enter bed location data using GUI 120. In this regard, when bed 12 is plugged into AC outlet 170 and casters 49 are braked, home screen 144 appears on GUI 120 but without window 142 appearing on screen 144 because there is not yet any room location associated with bed 12, as shown in the upper right region of FIG. 4A. In some embodiments, after bed 12 is plugged into outlet 170, a reminder screen appears on GUI 120 to remind the caregiver to brake casters 49 using foot pedals 51. In any event, once home screen 144 appears on GUI 120 as shown in FIG. 4A, the caregiver is able to select location button 150 to navigate to subsequent screens for manual entry of bed location information or data as described below.

If it is determined at block 218 that manual entry of bed location information has occurred within 30 seconds, then algorithm 210 ends as indicated at block 220. In other embodiments, a time threshold greater than or less than 30 seconds may be implemented at block 218 of algorithm 210. For example, a time threshold of 1 minute or even up to 2 minutes are within the scope of the present disclosure, just to give a couple of arbitrary examples. If it is determined at block 218 that location information has not been entered manually within 30 seconds of the bed 12 being plugged in and the casters 49 locked, then algorithm 210 proceeds to block 222 to play a voice prompt reminding the caregiver that bed location data needs to be manually entered using GUI 120. The voice prompt is implemented, for example, as a sound file stored in memory 114 and played through a speaker (not shown) of bed 12. The voice prompt includes a message such as, for example, "Bed not located. Please input location." Other audio prompts are within the scope of the present disclosure at the discretion of the bed designer or programmer.

After the voice prompt is played at block 222, or substantially simultaneously with playing the voice prompt at block 222, algorithm 210 causes a bed-not-located screen 224 to be displayed on GUI 120 as shown in FIG. 4A. Screen 224 includes a close button or icon 226 that is selected if the caregiver does not wish to manually enter location data into memory 114 of bed 12 for communication via module 16 to network 18. After button 226 is selected, home screen 144 is displayed on GUI 120. Screen 224 also includes an OK icon or button 228 that is selected to navigate to further screens for manual entry of bed location data or information as will be discussed in further detail below. In the illustrative example, screen 224 also displays the text string, "BED NOT SYNCHED WITH NURSE CALL SYSTEM. INPUT BED LOCATION."

Giving caregivers a threshold period of time for entry of manual location data at block 218 of algorithm 210 is an improvement over the algorithm depicted in FIG. 11 of U.S. Patent Application Publication No. 2018/0039743 A1 in which manual entry screens are displayed in response to AC power being applied to the bed. For example, the caregiver may wish to see other information on home screen 144 regarding bed status prior to beginning the process of manually entering bed location information. Furthermore, requiring bed 12 to be plugged in to an AC outlet 170 and requiring casters 49 to be locked or braked in algorithm 210 prior to display of bed-not-located also represents an improvement over the algorithm depicted in FIG. 11 of U.S. Patent Application Publication No. 2018/0039743 A1 because the two conditions of algorithm 210 at blocks 214, 216 provides redundant assurance that the bed 12 is intended to remain at its location for an extended period of time, thereby warranting manual entry of bed location information. Still further, the algorithm of FIG. 11 of U.S. Patent Application Publication No. 2018/0039743 A1 does not include any voice prompt like the algorithm 210 of the present disclosure. The voice prompt at block 222 of algorithm 210 assures that the caregiver is alerted to the need for manual entry of bed location information if the caregiver does not otherwise notice the bed-not-located screen 224 being displayed on GUI 120, for example.

In response to OK icon 228 being selected on screen 224, algorithm 210 causes a select-the-bed-location screen 230 being displayed on GUI 120 as shown in FIG. 4A. Screen 230 also appears on GUI 120 in response to location button 150 on home screen 144 being selected by the caregiver. Furthermore, screen 230 appears on GUI 120 in response to edit icon 148 of window 142, shown in FIG. 3, being selected on home screen 144. Thus, there are three ways in which screen 230 becomes displayed on GUI 120, as follows: selection of OK button 228 on screen 224; selection of location button 150 on screen 144; and selection of edit icon 148 of window 142, if shown, on screen 144. Regardless of the manner in which the caregiver navigates to screen 230, the remaining discussion below of screen 230 and the screens of FIG. 4B is equally applicable.

Screen 230 includes a table 232 having a list of room locations that can be selected by touching the row in the table 232 corresponding to the room in which bed 12 is located. An up arrow icon 234 and a down arrow icon 236 are provided on screen 230 in the right hand portion of table 232. Icons 234, 236 are touched by the caregiver to scroll up or down, respectively, to view other room location choices that are available for selecting by the caregiver on table 232. In the illustrative example of FIG. 4A, the location of MED/SURG 2011-A is selected in table 232 as indicated by the border highlighting around the selected row in table 232. A delete icon 238 is shown to the left of the selected bed location in table 232. Beneath table 232 of screen 230 is a campus edit icon or button 240 and a unit edit button or icon 242.

At the bottom of screen 230 is a cancel button or icon 244 and a select icon or button 246. If the caregiver does not wish to make any manual location selections, the cancel button 244 is selected and GUI 120 will return to showing home screen 144. If the room location of table 232 is the desired room location and if the desired campus and unit selections appear to the right of respective buttons 240, 242, the select button 246 is selected to store the room location, campus location, and unit location information in memory 114 of control circuitry 110 of bed 12. After the bed location information is stored in memory 114, control circuitry 110 controls wireless communication module 16 of bed 12 to transmit the bed location information to one or more of servers 22, 24, 26 of the corresponding systems 23, 25, 27 of network 18 via one or more WAP's 14.

In some embodiments, module 16 of bed 12 transmits the stored location information a single time and, if an acknowledgement message is returned to module 16 of bed via one or more WAP's 14 indicating that the desired destination server(s) 22, 24, 26 has successfully received the location information from bed 12, then module does not transmit the location information subsequently unless a change is made to the location information using GUI 120 or unless bed 12 is unplugged from outlet 170 for a threshold period of time in which case algorithm 210 starts anew at block 212. In such embodiments, a bed ID such as a bed serial number or MAC address is transmitted with the bed location information. During subsequent bed status data transmissions from bed 12, the bed ID is also transmitted and is used by the receiving server(s) 22, 24, 26 to correlate or associate the bed status information with the bed location information. In other embodiments, the bed location data is transmitted by module 16 of bed along with each transmission of bed status data after the bed location information has been stored in memory 114 of control circuitry 110.

If the caregiver wishes to select a different campus location while viewing screen 230, the campus icon 240 is selected on screen 230 of FIG. 4A and algorithm 210 proceeds to display a select-the-campus-location screen 248 on GUI 120 as shown in FIG. 4B. The line labeled with circle A shows the screen flow of algorithm 210 in this regard. Screen 248 includes a table 250 having a list of campus locations that can be selected by touching the row in the table 250 corresponding to the campus at which bed 12 is located. Up and down arrow icons 234, 236 are provided at the right hand portion of table 250 and are touched to scroll up or down, respectively, to view other campus location choices that are available for selecting by the caregiver on table 250. In the illustrative example of FIG. 4B, the campus of ST. ELIZABETH SOUTH is selected in table 250 as indicated by the border highlighting around the selected row in table 250.

Delete icon 238 is shown to the left of the selected campus location in table 250. Beneath table 250 of screen 248 is campus edit icon or button 240 and a unit edit button or icon 242. At the bottom of screen 248 is cancel button or icon 244 and select icon or button 246. Buttons 238, 240, 242, 244, 246 on screen 248 function in the same manner as these same buttons 238, 240, 242, 244, 246 function on screen 230. For example, if the caregiver does not wish to make any manual location selections on screen 248, the cancel button 244 is selected and GUI 120 will return to showing home screen 144 or, in some embodiments, screen 230. If the campus location of table 250 is the desired campus location and if the desired unit selection also appears to the right of button 242, the select button 246 is selected to store the campus location and unit location in memory 114 of control circuitry 110 of bed 12 for eventual transmission by module 16 as described above.

If the caregiver wishes to select a different unit location while viewing screen 230 or while viewing screen 248, the unit icon 242 is selected on screen 230 of FIG. 4A or screen 248 of FIG. 4B, as the case may be, and algorithm 210 proceeds to display a select-the-unit-location screen 252 on GUI 120 as shown in FIG. 4B. The line labeled with circle B shows the screen flow of algorithm 210 in this regard in connection with selection of button 242 on screen 230. Screen 252 also appears on GUI 120 in response to the caregiver selecting button 246 on screen 248. In either case, screen 252 includes a table 254 having a list of unit locations that can be selected by touching the row in the table 254 corresponding to the unit at which bed 12 is located. Up and down arrow icons 234, 236 are provided at the right hand portion of table 254 and are touched to scroll up or down, respectively, to view other unit location choices that are available for selecting by the caregiver on table 254. In the illustrative example of FIG. 4B, the unit of WEST TOWER is selected in table 254 as indicated by the border highlighting around the selected row in table 254.

Delete icon 238 is shown to the left of the selected unit location in table 254. Beneath table 254 of screen 252 is campus edit icon or button 240 and unit edit button or icon 242. At the bottom of screen 252 is cancel button or icon 244 and select icon or button 246. Buttons 238, 240, 242, 244, 246 on screen 252 function in the same manner as these same buttons 238, 240, 242, 244, 246 function on screens 230, 248. For example, if the caregiver does not wish to make any manual location selections on screen 252, the cancel button 244 is selected and GUI 120 will return to showing home screen 144 or, in some embodiments, return to showing screen 230. If the unit location of table 254 is the desired unit location and if the desired campus selection also appears to the right of button 240, the select button 246 of screen 252 is selected to store the campus location and unit location in memory 114 of control circuitry 110 of bed 12 for eventual transmission by module 16 as described above.

As noted above with regard to screen 230, if the room location of table 232 is the desired room location and if the desired campus and unit selections appear to the right of respective buttons 240, 242, the select button 246 is selected to store the room location, campus location, and unit location information in memory 114 of control circuitry 110 of bed 12. Selection of button 246 on screen 230 of FIG. 4A results in a modified start-up screen 140' appearing on GUI 120 as shown in FIG. 4B. The line labeled with circle C shows the screen flow of algorithm 210 in this regard in connection with selection of button 246 on screen 230. On screen 140', window 142 now shows text string 146 with the selected room location information, MED/SURG 2011-A in the illustrative example, that was chosen using table 232 of screen 230. Window 142 appears on screen 140' for a threshold period of time, such as 5 to 30 seconds, and then disappears as was described above.

While window 142 appears on screen 140', the caregiver has the option of selecting edit icon 148 to further edit the bed location information if desired. In response to selection of button 148 on screen 140', algorithm 210 causes a current-bed-location screen 256 to appear on GUI 120 as shown in FIG. 4B. Screen 256 includes a table 258 that indicates with border highlighting the current bed location that was selected previously. The caregiver can then make another selection on table 258 to change the room location information. Scroll arrows 234, 236 are provided in table 258 for use by the caregiver to scroll other room location options as noted above. Buttons 240, 242, 244, 246 appear on screen 256 and function in the same manner as described above. For example, selection of button 240 results in navigation to screen 248, selection of button 242 results in navigation to screen 252, selection of button 244 results in navigation back to screen 140', and selection of button 246 results in navigation back to screen 140' but with the new room location information manually selected on table 258 appearing as text string 146 in window 142.

In response to button 238 being selected on screen 256 of FIG. 4B, algorithm 210 causes screen 230 to, once again, be shown on GUI 120. The description above of screen 230 shown in FIG. 4A is equally applicable to screen 230 shown in FIG. 4B. Selection of button 238 on screen 230, be it the one shown in FIG. 4A or the one shown in FIG. 4B, results in a location delete screen 260 appearing on GUI 120. Thus, button 238 is selected when the caregiver wishes to delete a room location from even appearing on table 232. Screen 260 includes the following textual information: "ARE YOU SURE YOU WANT TO DELETE THIS LOCATION? RESTORING A LOCATION MUST BE DONE IN NURSE CALL SYSTEM." Screen 260 includes a yes button 262 that is selected if the caregiver does, indeed, wish to delete the selected bed location information from table 232 altogether. Screen 260 also includes a no button 264 that is selected to abort the deletion of the selected of the bed location information selected on table 232.

After either of buttons 262, 264 is selected on screen 260, algorithm 210 returns back to screen 230 so that the caregiver can, if desired, select the bed location information from among the remaining information on table 232 and then select icon 246, or the user can select icon 244 and return to screen 140' or screen 144 as the case may be.

Button 238 of screen 248 and button 238 of screen 252 operate in a substantially similar manner as button 238 of screen 230 except that selected campus location information or selected unit location information, as the case may be, are deleted from the respective tables 250, 254 by navigating to screen 260 and selecting the yes button 262.

Figure 5A:
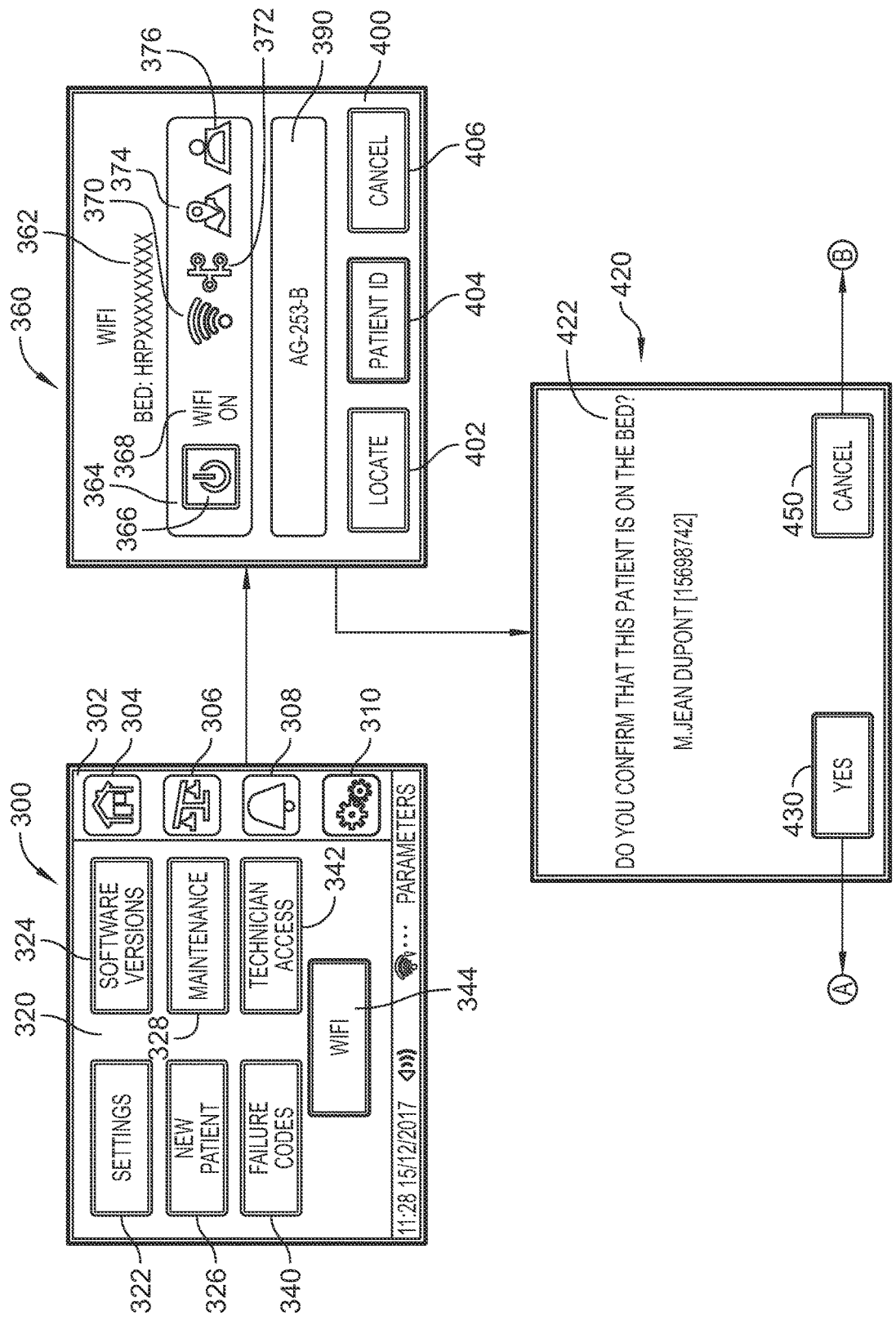
FIGS. 5A-5C together make up a diagrammatic view having screen flows showing how the GUI of the bed is used to manually enter patient identification data for the patient bed.
Figure 5B:
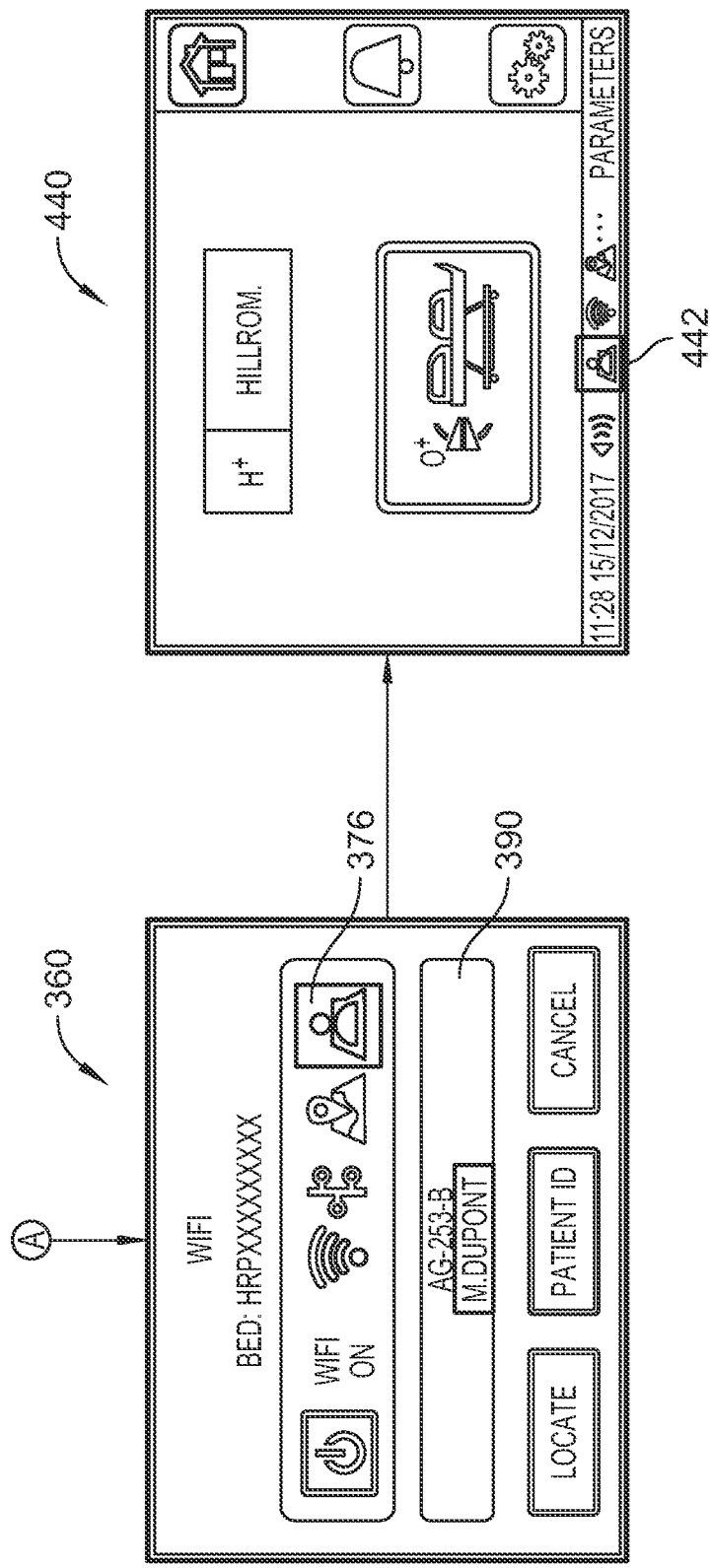
Figure 5C:
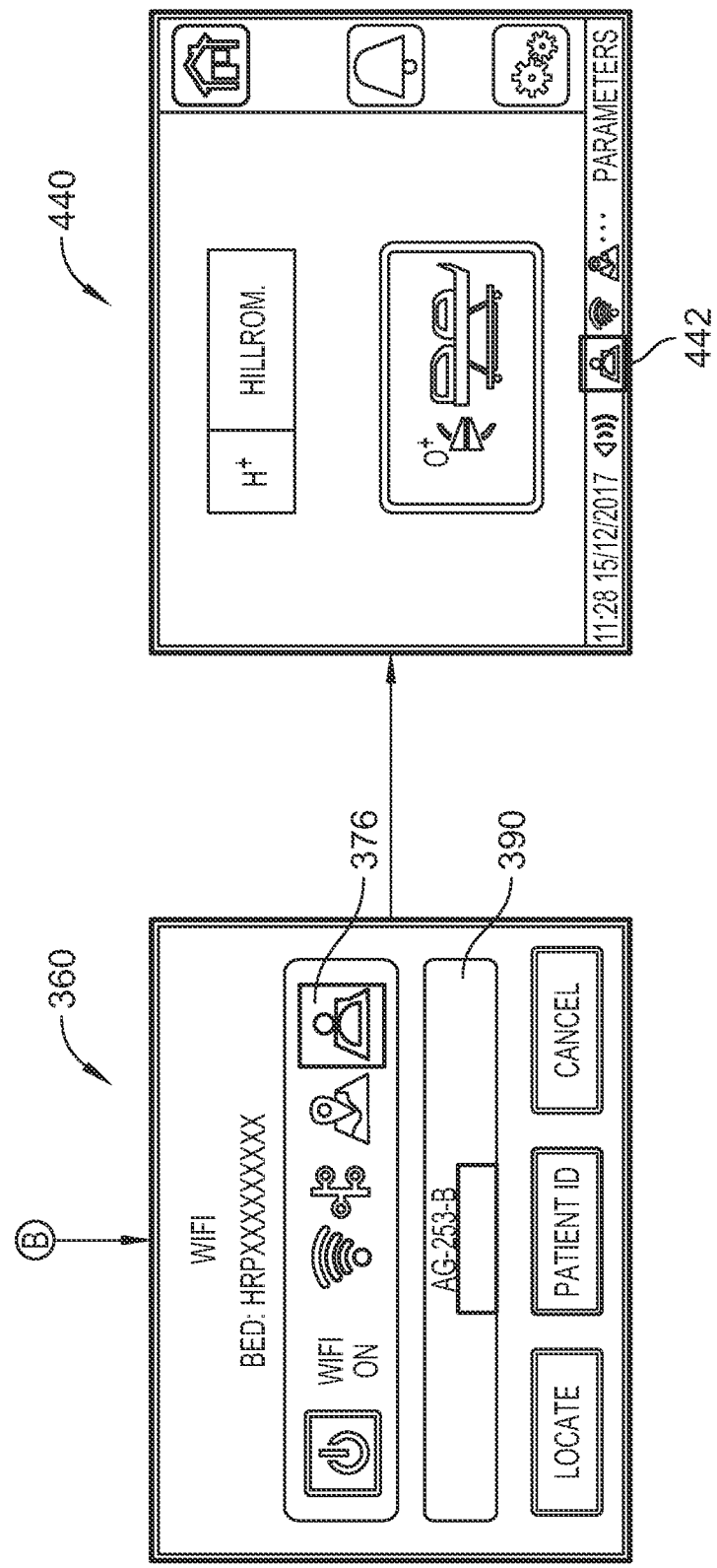

Referring now to FIGS. 5A-5C, a parameters screen 300 is shown on GUI 120. GUI 120 is embodied as a touch screen display having various icons or buttons that are selectable by a caregiver to navigate to other screens for selection of various bed functions and entry of various types of data as will be discussed below, primarily in connection with manual entry of patient identification data on GUI 120. Parameters screen 300 appears on GUI 120, in some embodiments, in response to a caregiver (or really, any user for that matter) touching GUI 120 to wake GUI 120 from a dormant state in which GUI 120 is blacked out or, in some embodiments, in which GUI 120 displays a screen saver image of some sort. In some embodiments, the parameters screen 300 is displayed by selecting a parameters button on a home screen or other screen. In some embodiments, the control circuitry 110 is configured to play a voice prompt to remind the caregiver to manually validate the patient identification data after a threshold period of time elapses after a remote server, such as an ADT server, an EMR server, bed status data server, or the like has communicated the patient name to the bed 12. In some embodiments, the threshold period of time begins after the patient enters the bed 12. In some embodiments, the threshold period of time begins after the caregiver awakens the GUI 120 from a sleep screen.

The parameters screen 300 includes a field 302 having icons and buttons that when selected navigate the user to various screens. A home button 304 is selectable, such as by touching, to navigate to a home or start screen. A weigh scale button 306 is selectable, such as by touching, to navigate to the screens that are used to provide information on a weight of the patient as measured by the scale system 70. An alarm button 308 is selectable, such as by touching, to navigate to an alarm screen that enables the user to set various alarms for the bed 12, e.g. a bed exit alarm. A settings button 310 is selectable, such as by touching, to navigate to various screens that enable bed settings to be adjusted, e.g. bed position settings.

The parameters screen 300 also includes a parameters field 320 having icons and buttons that, when selected, allow the user to adjust various parameters of the bed. For example, a settings button 322 is selectable, such as by touching, to navigate to various screens that enable the user to adjust various settings related to patient identification. A software verification button 324 is selectable, such as by touching, to navigate to a software screen were a user can verify that the software operating the control circuitry 110 is updated, loaded, and/or operational. A new patient button 326 is selectable, such as by touching, to navigate to a screen that allows the user to enter patient information related to a newly admitted patient, e.g. name, address, patient ID number, etc. A maintenance button 328 is selectable, such as by touching, to navigate to various maintenance screens that enable a technician to trouble-shoot and correct technical failures of the bed 12. A failure codes button 340 is selectable, such as by touching, to display a list of failure codes related to the bed 12. Such failure codes may be utilized to identify errors in the bed 12. A technician access button 342 is selectable, such as by touching, to provide a technician access to the software of the bed 12 so that maintenance can be performed. The technician access button 342 also allows a technician to set specific parameters related to the various functions of the bed 12, as described herein. A WiFi button 344 is selectable, such as by touching to navigate to a WiFi screen 360, wherein WiFi connectivity is validated.

Referring still to FIG. 5A, the WiFi screen 360 includes a bed field 362 that displays an identification number associated with the bed 12. Accordingly, a user may read this field to verify that the correct bed 12 is in use. A connectivity field 364 includes various icons that confirm connectivity of the bed 12. A power button 366 is selectable to turn the WiFi functions of the bed 12 on and off. The power button 366 is illuminated in a first color, e.g. green, to verify that the WiFi is turned on. The power icon 366 may be unilluminated on illuminated in a second color, e.g. red, if the WiFi is not turned on. A WiFi connection icon 368 reads "on" when the wireless communication module 16 is powered. The WiFi connection icon 368 may read "off" when the wireless communication module 16 is not powered. A signal strength icon 370 includes a plurality of bars that are illuminated to indicate a strength of a WiFi network connection. For example, the number of bars illuminated is directly proportional to a strength of the signal. That is, the more bars that are illuminated, the stronger the signal is. A server icon 372 is illuminated in a first color, e.g. green, to indicate that the bed 12 is connected to a server. If the bed 12 is not connected to a server, the server icon 372 may be unilluminated or illuminated in a second color, e.g. red.

A location icon 374 is illuminated in a first color, e.g. green, if bed location has been communicated to the bed 12 by the real-time locating system 25 or by manual entry of bed location using GUI 120 of the bed 12. The location icon 374 may be unilluminated or illuminated in a second color, e.g. red, if the location of the bed 12 has not been communicated to the bed 12 by the real-time locating system 25 or the bed 12 has not been located by manual entry. A patient identification icon 376 is provided to notify the caregiver whether the patient on the bed 12 is identified or validated. If the patient has been identified and/or validated, the patient identification icon 376 is illuminated in a first color, e.g. green. If the patient has not been identified or validated, the patient identification icon 376 is unilluminated or illuminated in a second color, e.g. red. The patient being validated involves a manual validation process by a user as will be described below.

A patient identification field 390 lists a name or patient number or other patient identifier of the patient on the bed 12. If the patient has not been identified, the patient identification field 390 is blank or simply lists the room number in which bed 12 is located as shown in FIG. 5A. WiFi screen 360 includes a data field 400 that includes various icons and buttons for selecting the location of the bed 12 and the identification of the patient. For example, a locate button 402 is selectable, such as by touching, to manually identify a room in which the bed is positioned, as described above. A patient ID button 404 is selectable, such as by touching, to navigate to a patient identification screen 420. A cancel button 406 is selectable, such as by touching, to return to the parameters screen 300. The patient identification screen 420 includes text 422 asking the user to verify or confirm that the listed patient is the actual patient on the bed 12. For example, the text 422 read "DO YOU CONFIRM THAT THIS PATIENT IS ON THE BED?" in the illustrative example. Below the text 422 the name of a patient and/or a patient ID number is listed.

The listed name of the patient below text 422 may be the name of the patient most recently received from a hospital server. In some embodiments, the listed name of the patient may be the name of the last patient to have been confirmed to be on the bed 12. In other embodiments, the listed patient name is the name of a patient that has been newly assigned to the bed 12 and communicated to the bed 12 from a remote server such as an ADT server, EMR server 26, bed status data server, or the like. In some embodiments, the patient room assignment for each patient is entered at an ADT computer at the time of patient admission and then, the associated ADT server sends the patient identification (ID) and location ID to the bed status data server which, in turn, determines the bed ID of the bed 12 at the location corresponding to the location ID. The bed status data server then communicates the patient ID to the bed 12 for inclusion on the screen 420 beneath the text 422.

A yes button 430 is selectable, such as by touching, to verify/confirm that the patient listed in the text 422 is the patient on the bed 12. Selecting the yes button 430 returns the user to the WiFi Sceen 360, as shown in FIG. 5B. As illustrated in FIG. 5B, at this stage, the patient name and identification number is shown in the patient identification field 390. Also, the patient identification icon 376 is illuminated in the first color. FIG. 5B also illustrates a home screen 440 that is displayed after the home button 304 is selected. Once the patient identification is verified, the home screen 440 illuminates a patient identification icon 442, similar to patient identification icon 376.

The patient identification screen 420 also includes a cancel button 450 that is selectable, such as by touching, when the identification of the patient cannot be confirmed or, for some reason, the caregiver or user decides not to confirm the identification of the patient. In some embodiments, the cancel button 450 may be a no button. Selecting the cancel button 450 returns the user to the WiFi Sceen 360, as shown in FIG. 5C. As illustrated in FIG. 5C, at this stage, the patient name and/or identification number are not shown in the patient identification field 390 but the room number still appears in the field 390. Also, the patient identification icon 376 is either unilluminated or illuminated in the second color. FIG. 5C also illustrates the home screen 440 that is displayed after the home button 304 is selected. When the patient identification is not verified, the home screen 440 does not illuminate the patient identification icon 442 or the patient identification icon 442 is illuminated in the second color.

Figure 6:
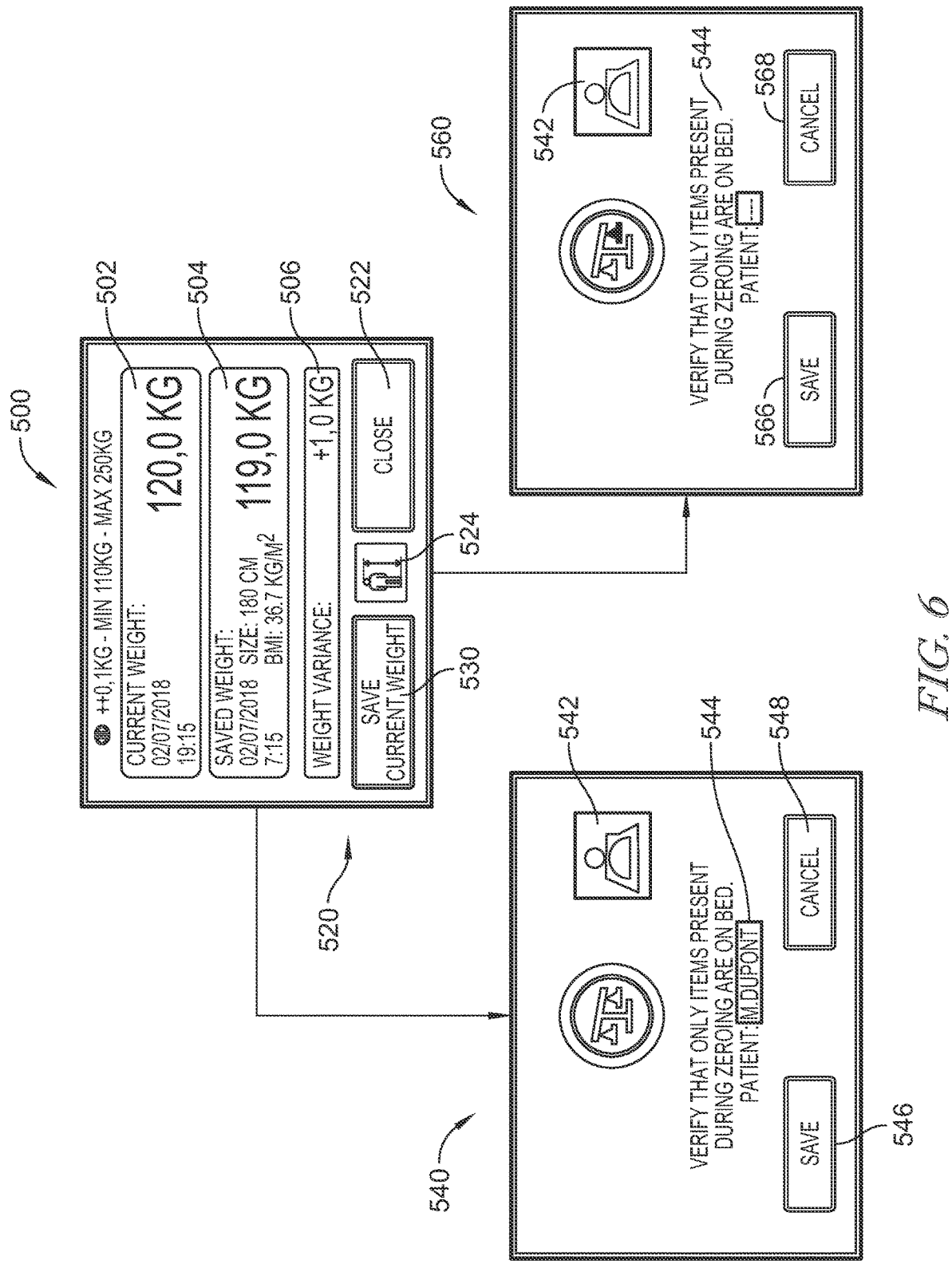
FIG. 6 is a diagrammatic view having screen flows showing how the GUI of the bed is used to enter patient weight data for the patient bed.

FIG. 6 illustrates a weight input screen 500 that includes a current weight field 502. The current weight field 502 displays a current weight of the patient on the bed 12 as measured by the scale system 70. A saved weight field 504 displays a previously saved weight of the patient on the bed 12. The current weight and the saved weight are displayed in kilograms; however, the settings of the GUI 120 may be altered to display the current weight and the saved weight in other units such as pounds. A variance field 506 displays a change in the patient's weight from the saved weight to the current weight. Accordingly, the caregiver may track and record changes in the patient's weight.

An input field 520 includes various icons and buttons that are selectable, such as by touching, to record data related to the patient's weight. A close button 522 closes the weight input screen 500 and returns the user to the home screen 440 or a previously opened screen. A height button 524 is selectable to enter the height of the patient. Accordingly, the height of the patient may be saved in electronic medical record 27. Additionally, by entering the patient height and patient weight, circuitry 110 of bed 12 is able to calculate a body mass index (BMI) of the patient on the bed 12.

A save current weight button 530 is selectable, to save the current weight in the electronic medical record system 27. By selecting the save current weight button 530, one of two screens is displayed depending upon whether the identification of the patient has been verified prior to taking the patient's weight. If the patient has been verified, as set forth above, the save weight screen 540 is displayed on the GUI 120. The save weight screen 540 includes a patient identification icon 542 that is illuminated in a first color, e.g. green, to indicate that the weight is being saved for the verified patient. A text field 544 displays text that reads "VERIFY THAT ONLY ITEMS PRESENT DURING ZEROING ARE ON BED." The text field also displays the patient name and, in some embodiments, patient identification number. Accordingly, the caregiver may select a save button 546 to take a verified patient weight reading when the patient identification has been verified. Conversely, the caregiver may select a cancel button 548 if other objects have been added to, or removed from, the bed 12 subsequent to zeroing or taring the scale system 27, or if the patient listed is not the correct patient.

Selection of the save button 546 results in transmission of the weight data tagged with the patient identification data to the electronic medical record system 27 for storage in the patient's electronic medical record. Selection of the save button 546 also results in storing, locally, in the bed memory, the patient weight thereby allowing the current weight to be compared to the previously stored weight. In some embodiments, the weight and verified patient ID data is transmitted first to the bed status data server and then from the bed status data server to the EMR server 26 of system 27. In some embodiments, module 16 of bed 12 transmits the weight data tagged with the patient identification data a single time and, if an acknowledgement message is returned to module 16 of bed via one or more WAP's 14 indicating that the electronic medical record system 27 has successfully received the weight data tagged with the patient identification data from bed 12, then module 16 does not transmit the location information subsequently unless a change is made to the weight data or to the patient identification data using GUI 120 or unless bed 12 is unplugged from outlet 170 for a threshold period of time in which case the patient identification data and the weight data must be reverified. In such embodiments, a bed ID such as a bed serial number or MAC address is transmitted with the weight data tagged with the patient identification data. During subsequent bed status data transmissions from bed 12, the bed ID is also transmitted and is used by the bed status data server and/or the electronic medical server 26 to correlate or associate the weight data tagged with the patient identification data with the bed location information. In other embodiments, the weight data tagged with the patient identification data is transmitted by module 16 of bed 12 along with each transmission of bed status data after the bed location information has been stored in memory 114 of control circuitry 110.

If the patient has not been identified, as set forth above, the save weight screen 560 is displayed on the GUI 120 in response to selection of the button 530 on the screen 500. The save weight screen 560 includes the patient identification icon 542 that is unilluminated or illuminated in a second color, e.g. red, to indicate that the weight is being saved for an unidentified patient. A text field 544 displays text that reads "VERIFY THAT ONLY ITEMS PRESENT DURING ZEROING ARE ON BED." In this scenario, the text field 544 does not identify a patient. Accordingly, the caregiver may select a save button 566 to take an unverified weight reading when the patient identification has not been verified. Conversely, the caregiver may select a cancel button 568 if other objects have been added to, or removed from, the bed 12 subsequent to zeroing or taring the scale system 27.

Selection of the save button 566 results in transmission of the weight data without patient identification data to the bed status data server and/or to EMR server 27 of the EMR system 27. In some embodiments, the weight data may be tagged with location identification data or bed identification data. In some embodiments, module 16 of bed 12 transmits the weight data a single time and, if an acknowledgement message is returned to module 16 of bed via one or more WAP's 14 indicating that the electronic medical record system 27 has successfully received the weight data from bed 12, then module does not transmit the location information subsequently unless a change is made to the weight data using GUI 120 or unless bed 12 is unplugged from outlet 170 for a threshold period of time in which case the weight data must be reverified. In such embodiments, a bed ID such as a bed serial number or MAC address is transmitted with the weight data. During subsequent bed status data transmissions from bed 12, the bed ID is also transmitted and is used by the bed status data server and/or the EMR server 26 to correlate or associate the weight data with the bed location information. In other embodiments, the weight data is transmitted by module 16 of bed 12 along with each transmission of bed status data after the bed location information has been stored in memory 114 of control circuitry 110.

Figure 7:
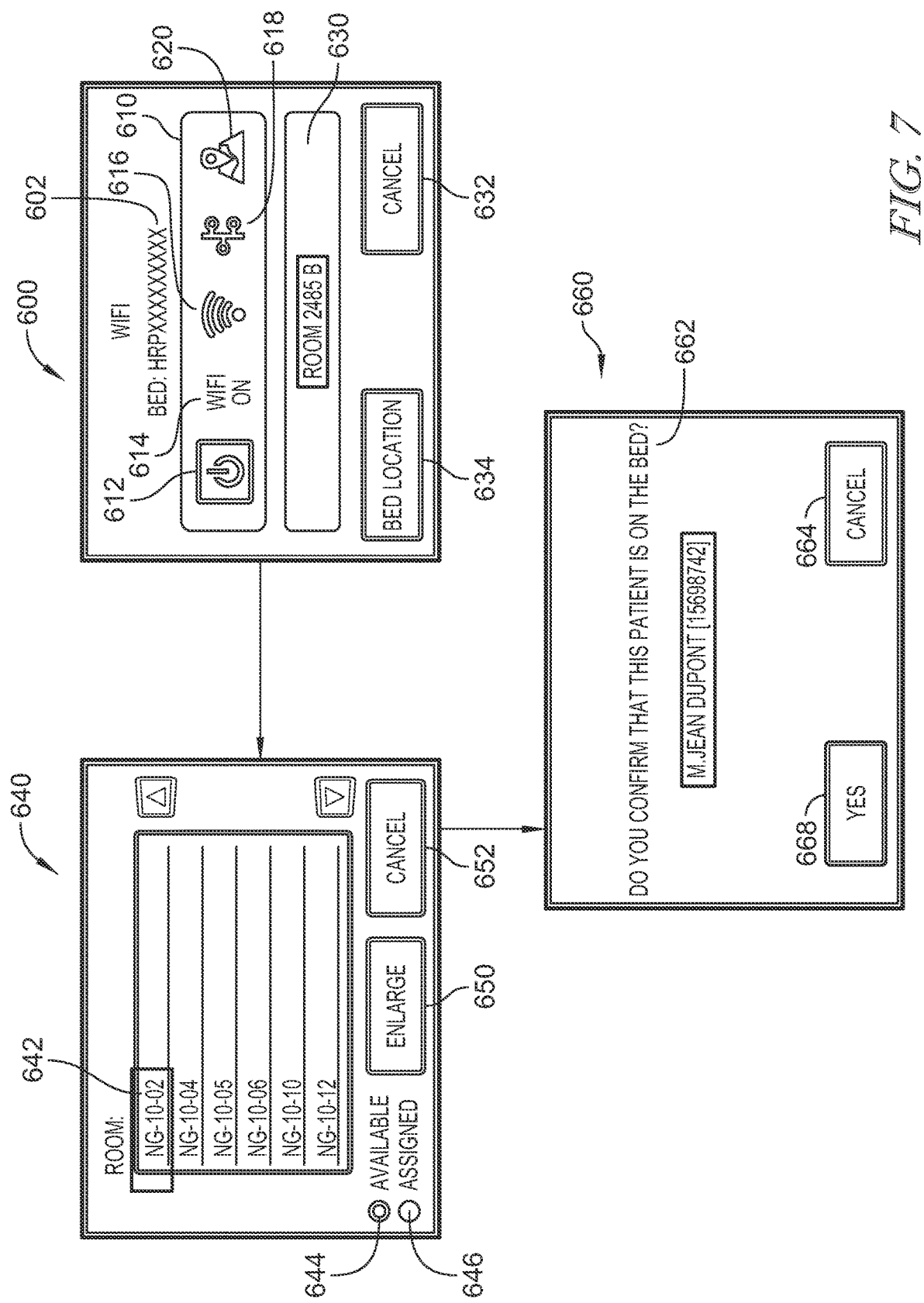
FIG. 7 is a diagrammatic view having screen flows showing how the GUI of the bed is used to enter patient identification data for the patient bed.

Referring now to FIG. 7, another example of a WiFi screen 600 includes a text box 602 that displays the bed identification number. A connectivity field 610 includes various icons that confirm connectivity of the bed 12. A power button 612 is illuminated in a first color, e.g. green, to verify that the bed 12 is connected to a WiFi network. The power button 612 may be unilluminated on illuminated in a second color, e.g. red, if the bed 12 is not connected to a WiFi network. WiFi connection icon 614 reads "on" when the wireless communication module 16 is powered. The WiFi connection icon 614 may read "off" when the wireless communication module 16 is not powered. A signal strength icon 616 includes a plurality of bars that are illuminated to indicate a strength of the network connection. For example, the number of bars illuminated is directly proportional to a strength of the signal. That is, the more bars that are illuminated, the stronger the signal is. A server icon 618 is illuminated in a first color, e.g. green, to indicate that the bed 12 is connected to a server. If the bed 12 is not connected to server the server icon 618 may be unilluminated or illuminated in a second color, e.g. red. A location icon 620 is illuminated in a first color, e.g. green, if bed location has been communicated to the bed 12 by the real-time locating system 25 or by manual entry of bed location. The location icon 620 may be unilluminated or illuminated in a second color, e.g. red, if the location of the bed 12 has not been communicated to the bed 12 by the real-time locating system 25 or the bed 12 has not been located by manual entry.

A room text box 630 displays the room number in which the bed 12 is positioned. If a room number has not been assigned to the bed 12, the room text box 630 is blank. A cancel button 632 is selectable, such as by touching, to cancel the WiFi screen 600 and return to the home screen 440. A bed location button 634 is selectable, such as by touching to initiate the process of associating a room number to the bed 12. Selection of the bed location button 634 results in a room selection screen 640 having a list 642 of rooms in the healthcare facility being displayed on the GUI 120. By selecting an available button 644, all rooms available in the healthcare facility are displayed in the list 642. The list may be scrolled through by scrolling with a finger on the GUI 120. If desired, up and down arrow buttons provided on the screen 640 to the right of the list 642 may be used for scrolling instead. Selecting an assigned button 646 populates the list 642 with all rooms in the healthcare facility that have been assigned to respective patients. The user may select a room number from the list 642, such as by touching the screen. An enlarge button 650 is selectable, such as by touching, to navigate one level up in a hierarchy, e.g. room, floor, building. A cancel button 652 is selectable, such as by touching, to return to the WiFi screen 600, the home screen 440, or any other previously displayed screen.

Selection of a room number from the list 642 navigates the user to a patient identification screen 660. The patient identification screen 660 includes a text box 662 that reads, "DO YOU CONFIRM THAT THIS PATIENT IS ON THE BED?" A patient name is provided beneath the text box 662. The user can select, such as by touching, a cancel button 664 if the user cannot confirm the identification of the patient on the bed 12 or, for some reason, the caregiver or user decides not to confirm the identification of the patient. Selection of the cancel button 664 returns the user to a previous screen without patient identification data. In some embodiments, the cancel button 664 is a no button. Selection of a yes button 668, for example by touching, confirms that the named patient is on the bed 12 and results in the transmission of patient identification data to the electronic medical record system 27 either directly or via the bed status data server.

Figure 8:
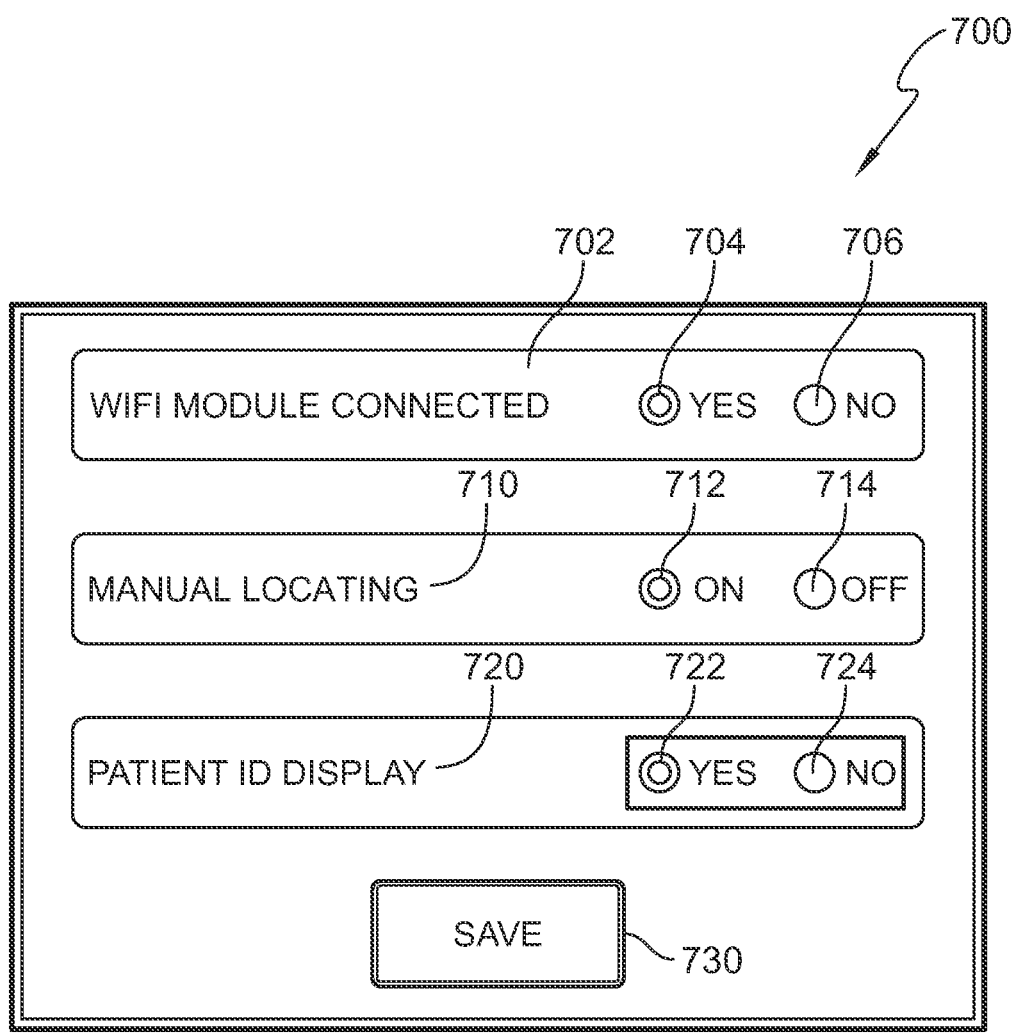
FIG. 8 is a diagrammatic view of a screen showing how the GUI of the bed is used to adjust settings.

Referring now to FIG. 8, a change configuration screen 700 is displayed on GUI 120 in response to selecting the settings button 322 on the parameters screen 300. The change configuration screen 700 includes a field 702 that reads, "WIFI MODULE CONNECTED." A yes button 704 and a no button 706 are displayed in the field 702. Selection of the yes button 704 results in the wireless module 16 connecting to the communication infrastructure 18 in which case fields 368, 614 indicate "WIFI ON." Selection of the no button 706 disconnects the wireless module 16 from the communication infrastructure 18 in which case fields 368, 614 indicate "WIFI OFF." Selection of the no button 706 also disables all screen related to connectivity. Selection of the no button 706 means that the bed is not equipped with a communication module, therefore, all connectivity screens would have no effect. A module (when present) can be turned on or off using button 366 (shown in FIG. 5A). The change configuration screen 700 includes another field 710 that reads, "MANUAL LOCATING." An on button 712 and an off button 714 are displayed in the field 710. Selection of the on button 712 configures the bed 12 to permit the caregiver to select the bed location manually as described above. Selection of the off button 714 disables the manual location selection feature from being usable on the bed 12. The change configuration screen 700 also includes a field 720 that reads, "PATIENT ID DISPLAY." A yes button 722 and a no button 724 are displayed in the field 720. Selection of the yes button 722 causes the GUI 120 to display the patient identification icon 376 for use in verifying the patient identification as described above. Selection of the no button 724 causes the patient identification icon 376 to not be displayed on the GUI 120 thereby disabling the patient identification verification feature from being usable on the bed 12. A Save button 730 is selectable, such as by touching, to save the settings.

In some embodiments, the user may enter any one of location data, patient identification data, and weight data using the GUI 120 of the bed 12. For example, the user may enter one of location data, patient identification data, and weight data, in some embodiments. In some embodiments, the user may enter any two of location data, patient identification data, and weight data. In some embodiments, the user may enter all three of location data, patient identification data, and weight data.

In some embodiments, the patient identification data may be temporarily invalidated. For example, the patient identification data may be temporarily invalidated in response to the wireless connection being lost, e.g. if the wireless connection is lost for over a predetermined period of time. In some embodiments, the patient identification data may be temporarily invalidated in response to the bed 12 being unplugged from the outlet 170 of the healthcare facility, e.g. if the bed 12 is unplugged from the outlet for longer than a predetermined period of time such as about ten seconds to about one minute. Optionally, the patient identification data may be temporarily invalidated in response to the patient exiting the bed 12, e.g. if the patient has exited the bed 12 for longer than a predetermined period of time.

Figure 9:
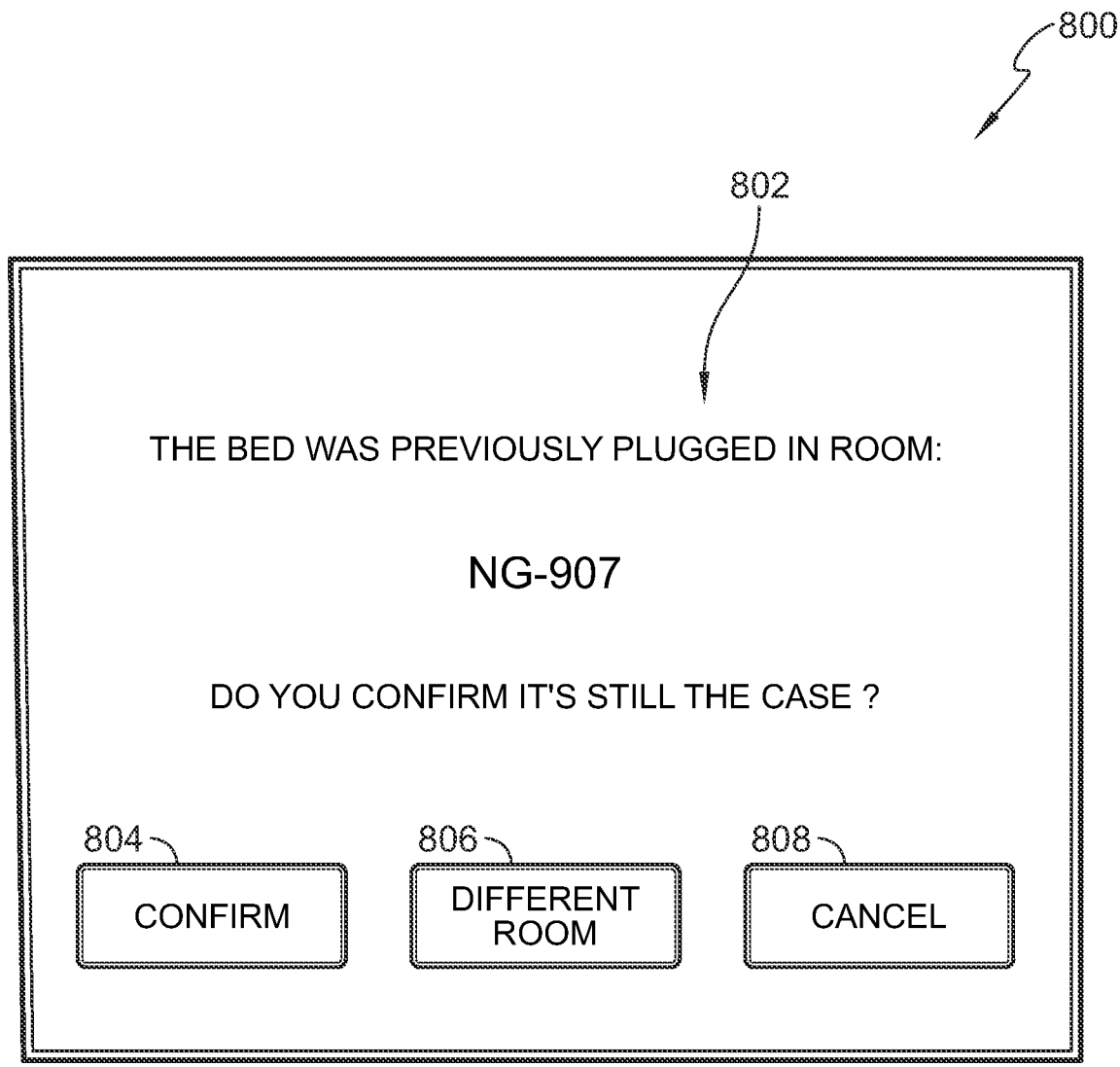
FIG. 9 is a diagrammatic view of a revalidation screen for revalidating location information.

When the patient identification data is temporarily invalidated, the patient identification data may be revalidated upon the conclusion of the temporary invalidating event. For example, if the wireless connection is reconnected, the patient identification data may be revalidated. In another example, if the bed is plugged back in, the patient identification data may be revalidated. In some embodiments, if the patient reenters the bed 12, the patient identification data may be revalidated. In some embodiments, the caregiver is prompted to revalidate the patient identification data. For example, the caregiver may be directed to a location revalidation screen 800, as illustrated in FIG. 9. The revalidation screen 800 includes a text box 802 that states the room that the bed 12 was previously plugged into and asks the caregiver to confirm whether the bed 12 is still plugged into that room. A confirm button 804 is selectable to confirm that the bed is still plugged into the stated room. A different room button 806 navigates the user to the screen 640 (shown in FIG. 7) to enable the user to select another room. A cancel button 808 returns the user to a home screen. In some embodiments, the revalidation screen is similar to the WiFi screen 360. In some embodiments, an alarm is triggered if the bed 12 is disassociated from its location.

In some embodiments, the patient identification data may be permanently invalidated. That is, the patient identification data may be invalidated in response to an invalid patient ID being entered. The patient identification data of a previously validated patient may be invalidated during the process of entering a new patient identification using the new patient button 326, in some embodiments. In some embodiments, the patient identification data may be invalidated in response to unplugging the bed 12 from AC power such as when the bed 12 is being transported, e.g. moved to another room. Optionally, the patient identification data of a previously validated patient may be invalidated when a new patient ID becomes available such as if a new patient is assigned to the bed 12 using an ADT system computer and the bed 12 receives the new patient data. If desired, the patient identification data is invalidated in response to new localization data being available from the real-time locating system 25 or entered manually on the GUI 120 of bed 12. In some embodiments, the patient identification data may be invalidated in response to a configuration of the settings being changed using the change configuration screen 700. The patient identification data may be invalidated in response to the patient exiting the bed 12 for longer than a predetermined period of time such as, for example, about 2 minutes to about 20 minutes such as for toileting, in some embodiments. After invalidation, the caregiver is prompted to revalidate the patient identification data. For example, the caregiver may be directed to the location revalidation screen 800. In some embodiments, the revalidation screen is similar to the WiFi screen 360. In some embodiments, an alarm is triggered if the bed 12 is disassociated from its location.

Although certain illustrative embodiments have been described in detail above, variations and modifications exist within the scope and spirit of this disclosure as described and as defined in the following claims.

The invention claimed is:

1. A patient bed comprising
a frame configured to support a patient,
circuitry carried by the frame, and
a graphical user interface (GUI) carried by the frame and coupled to the circuitry, the circuitry being configured to command the graphical user interface to display at least one user interface screen that is usable by a caregiver to manually enter location data indicative of a location in a healthcare facility at which the patient bed is located, the circuitry being configured to transmit the location data entered by the caregiver and a bed identification (ID) from the bed, wherein the circuitry is configured to command the GUI to display a first screen of the at least one interface screen that is used by the caregiver to manually enter location data,
wherein the circuitry is configured to prompt the caregiver to manually enter the location data of the patient bed after a threshold period of time elapses subsequent to a power plug of the circuitry being plugged into an outlet of a healthcare facility and subsequent to casters of the frame being braked.

2. The patient bed of claim 1, wherein the location data comprises a room number of the healthcare facility.

3. The patient bed of claim 1, wherein the GUI includes a change location button that is selectable by the caregiver to initiate a change of the location data prior to the threshold period of time elapsing.

4. The patient bed of claim 3, wherein a room menu screen appears on the GUI in response to the change location button being selected, the room menu screen permitting the caregiver to select a room number from a list of room numbers.

5. The patient bed of claim 3, wherein a campus icon and a unit icon appears on the GUI in response to the change location button being selected, the campus icon being selectable to cause a campus menu list being displayed on the GUI and the unit icon being selectable to cause a unit menu list being displayed on the GUI.

6. The patient bed of claim 1, wherein the first screen appearing on the GUI after the threshold period of time elapses includes a button that is selectable to initiate manual entry of the location data.

7. The patient bed of claim 6, wherein a room menu screen appears on the GUI in response to the button being selected on the first screen, the room menu screen permitting the caregiver to select a room number from a list of room numbers.

8. The patient bed of claim 6, wherein a campus icon and a unit icon appears on the GUI in response to the button being selected on the first screen, the campus icon being selectable to cause a campus menu list being displayed on the GUI and the unit icon being selectable to cause a unit menu list being displayed on the GUI.

9. The patient bed of claim 1, wherein the circuitry includes a wireless communication module configured to wirelessly transmit the location data and the bed ID to a wireless access point for delivery to at least one remote computer for purposes of making a bed-to-room association.

10. The patient bed of claim 9, wherein the wireless communication module also is configured to transmit bed status data from the bed.

11. The patient bed of claim 1, wherein the circuitry is configured to play a voice prompt to remind the caregiver to manually enter the location data after the threshold period of time elapses.

12. The patient bed of claim 1, wherein the circuitry is configured to command the GUI to display a patient verification screen that is usable by the caregiver to verify an identity of a patient supported on the patient bed.

13. A patient bed comprising
a frame configured to support a patient,
circuitry carried by the frame, and
a graphical user interface (GUI) carried by the frame and coupled to the circuitry, the circuitry being configured to command the graphical user interface to display at least one user interface screen that is usable by a caregiver to manually enter location data indicative of a location in a healthcare facility at which the patient bed is located, the circuitry being configured to transmit the location data entered by the caregiver and a bed identification (ID) from the bed,
wherein the circuitry is configured to annunciate a voice prompt to the caregiver to manually enter the location data of the patient bed after a threshold period of time elapses subsequent to a power plug of the circuitry being plugged into an outlet of a healthcare facility and subsequent to casters of the frame being braked.

14. The patient bed of claim 13, wherein the circuitry also commands the GUI to display a first screen of at least one interface screen that is used by the caregiver to manually enter location data after the threshold period of time elapses.

15. The patient bed of claim 14, wherein the location data comprises a room number.

16. The patient bed of claim 14, wherein the first screen appearing on the GUI includes a button that is selectable to initiate manual entry of the location data.

17. The patient bed of claim 16, wherein a room menu screen appears on the GUI in response to the button being selected on the first screen, the room menu screen permitting the caregiver to select a room number from a list of room numbers.

18. The patient bed of claim 16, wherein a campus icon and a unit icon appears on the GUI in response to the button being selected on the first screen, the campus icon being selectable to cause a campus menu list being displayed on the GUI and the unit icon being selectable to cause a unit menu list being displayed on the GUI.

19. The patient bed of claim 15, wherein the circuitry includes a wireless communication module configured to wirelessly transmit the location data and the bed ID to a wireless access point for delivery to at least one remote computer for purposes of making a bed-to-room association.

20. The patient bed of claim 19, wherein the wireless communication module also transmits bed status data from the bed.

21. The patient bed of claim 14, wherein the circuitry is configured to command the GUI to display a patient verification screen that is usable by the caregiver to verify an identity of a patient supported on the patient bed.

22. The patient bed of claim 13, wherein the GUI includes a change location button that is selectable by the caregiver to initiate a change of the location data prior to the threshold period of time elapsing.

23. The patient bed of claim 22, wherein a room menu screen appears on the GUI in response to the change location button being selected, the room menu screen permitting the caregiver to select a room number from a list of room numbers.

24. The patient bed of claim 22, wherein a campus icon and a unit icon appears on the GUI in response to the change location button being selected, the campus icon being selectable to cause a campus menu list being displayed on the GUI and the unit icon being selectable to cause a unit menu list being displayed on the GUI.

* * * * *